United States Patent
Siepis et al.

(10) Patent No.: US 9,730,893 B2
(45) Date of Patent: Aug. 15, 2017

(54) LIPID ASSEMBLIES COMPRISING ANIONIC LYSOLIPIDS AND USE THEREOF

(71) Applicant: BIOMEDICAL RESEARCH FOUNDATION OF THE ACADEMY OF ATHENS, Athens (GR)

(72) Inventors: Evgenios Siepis, Frenaros (GR); Evangelos Andreakos, N. Psychiko (GR)

(73) Assignee: BIOMEDICAL RESEARCH FOUNDATION OF THE ACADEMY OF ATHENS, Athens (GR)

( * ) Notice: Subject to any disclaimer, the term of this patent is extended or adjusted under 35 U.S.C. 154(b) by 0 days.

(21) Appl. No.: 14/425,830

(22) PCT Filed: Sep. 5, 2013

(86) PCT No.: PCT/EP2013/068359
§ 371 (c)(1),
(2) Date: Mar. 4, 2015

(87) PCT Pub. No.: WO2014/037436
PCT Pub. Date: Mar. 13, 2014

(65) Prior Publication Data
US 2015/0216803 A1    Aug. 6, 2015

(30) Foreign Application Priority Data
Sep. 6, 2012 (GR) ............... 20120100446

(51) Int. Cl.
*A61K 9/127* (2006.01)
*C12N 15/113* (2010.01)

(52) U.S. Cl.
CPC ............ *A61K 9/1274* (2013.01); *A61K 9/127* (2013.01); *C12N 15/113* (2013.01); *C12N 2310/14* (2013.01)

(58) Field of Classification Search
None
See application file for complete search history.

(56) References Cited

FOREIGN PATENT DOCUMENTS

| WO | 2006/048329 | 5/2006 |
|----|-------------|--------|
| WO | 2006/053646 | 5/2006 |
| WO | 2007/064857 | 6/2007 |

OTHER PUBLICATIONS

Stark, et al. (2007) "Association of vasoactive intestinal peptide with polymer-grafted liposomes: Structural aspects for pulmonary delivery", Biochimica et Biophysica Acta (BBA)—Biomembranes, 1768(3): 705-14.*
Tycko, 2000, "Epigenetic gene silencing in cancer", The Journal of Clinical Investigation, 105(4): 401-07.*
Stower (2011) "Human Genetics: Pleiotropic mutations", Nature Reviews Genetics, 13: nrg3132, 1 page long.*
Lesage (2009) "Parkinson's disease: from monogenic forms to genetic susceptibility factors", Human Molecular Genetics, 18(1): R48-R59.*
Bagby, et al. (2012) "Impact of Molecular Weight on Lymphatic Drainage of a Biopolymer-Based Imaging Agent", Pharmaceutics, 4: 276-95.*
International Search Report dated Feb. 6, 2014 from International Application No. PCT/EP2013/068359, pp. 1-3.

* cited by examiner

*Primary Examiner* — Robert M Kelly
(74) *Attorney, Agent, or Firm* — MH2 TECHNOLOGY LAW GROUP, LLP

(57) ABSTRACT

The present invention relates to lipid assemblies, compositions, and liposomal delivery systems comprising single chain anionic lipids, and the use thereof in diagnosis and therapy. It involves the use of anionic lysolipids for modifying the surface charge of a cationic lipid composition consisting at least one type of cationic lipid, optionally in combination with one or more neutral lipids and/or one or more anionic lipids.

23 Claims, 8 Drawing Sheets

FIGURE 2
SALINE
Free siRNA
FORMULATION I
FORMULATION II
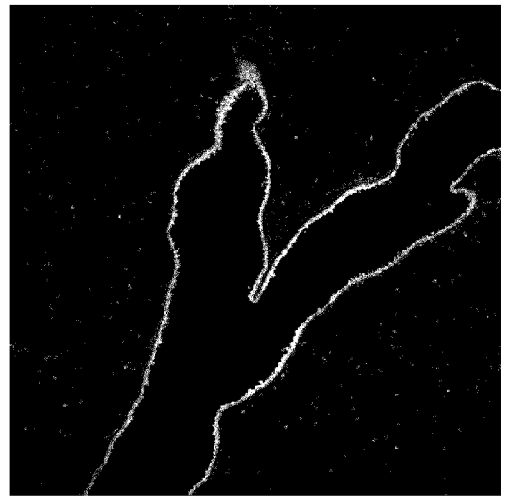

FIGURE 3
SALINE
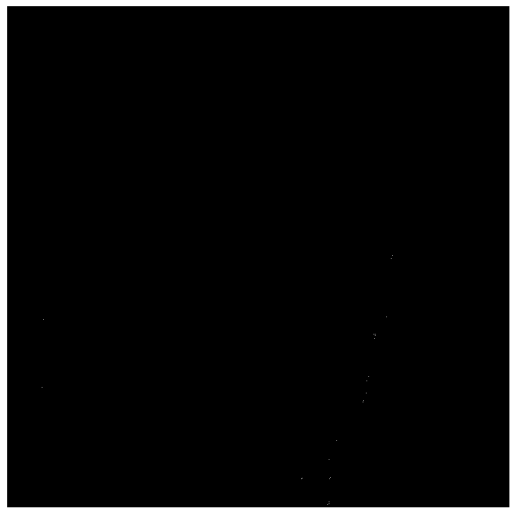
Free siRNA
FORMULATION I
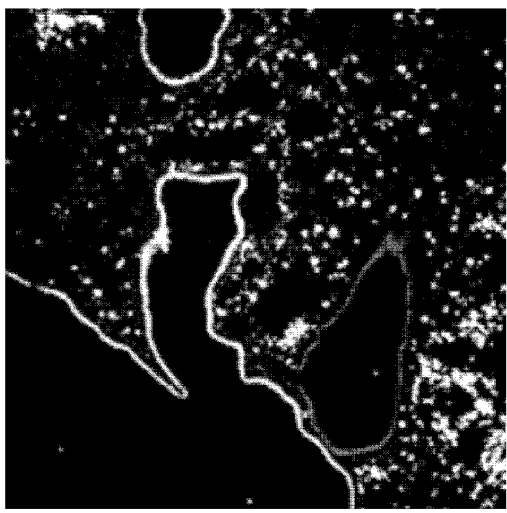
FORMULATION II
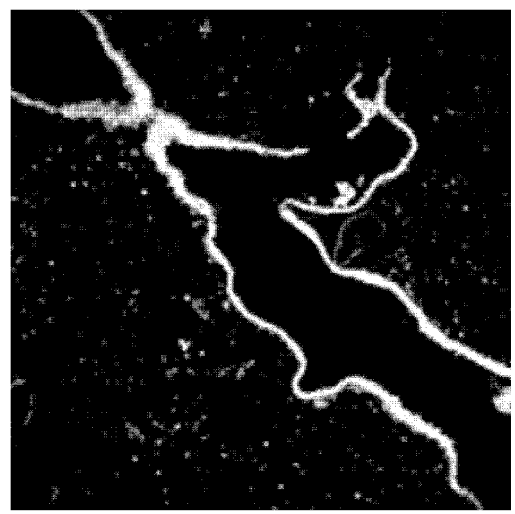

FIGURE 7
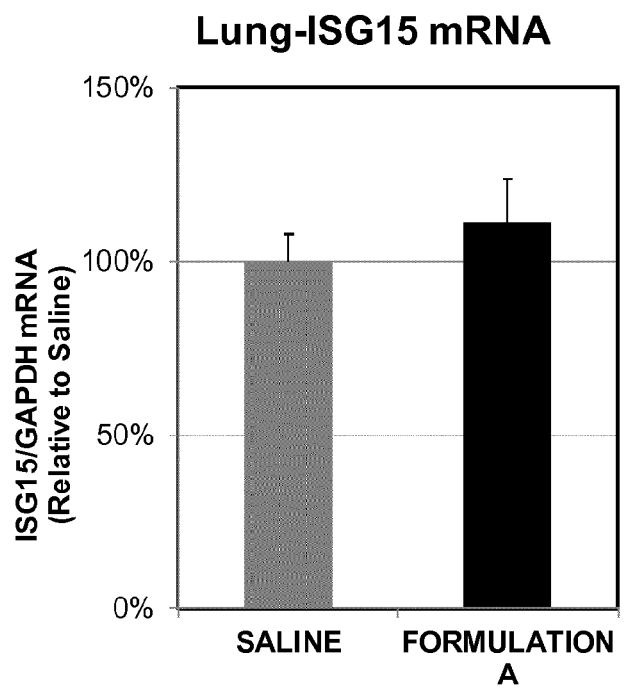
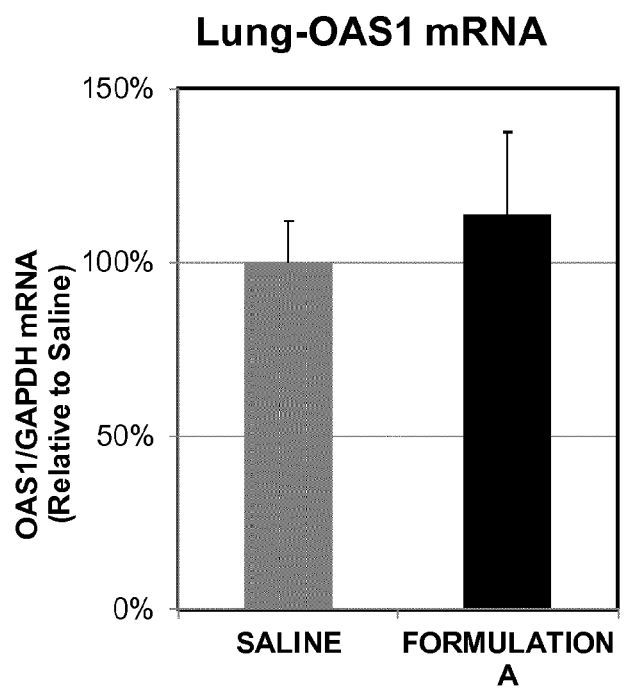

FIGURE 8
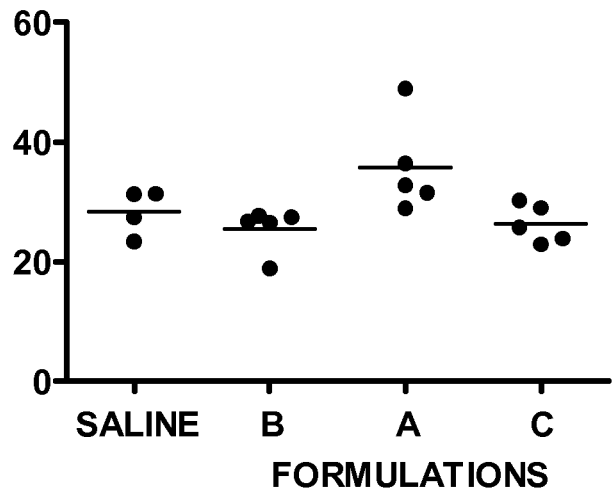
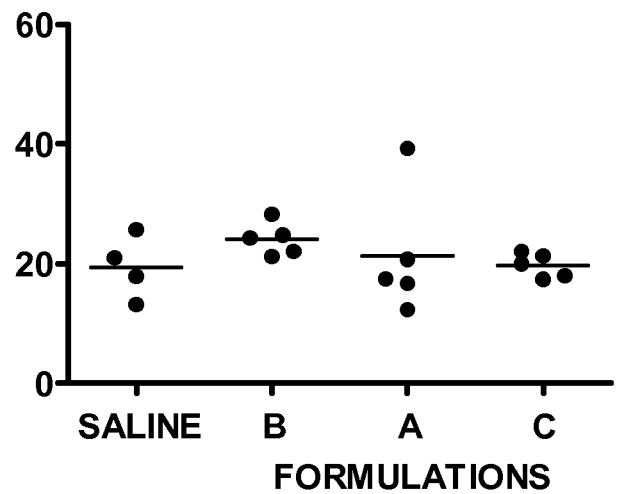

LIPID ASSEMBLIES COMPRISING ANIONIC LYSOLIPIDS AND USE THEREOF

CROSS-REFERENCE TO RELATED APPLICATIONS

This application is a U.S. National Stage application of PCT/EP2013/068359 filed 5 Sep. 2013, which claims priority to Greek patent application 20130100446 filed 6 Sep. 2012, the entire disclosures of which are hereby incorporated herein by reference in their entireties.

FIELD OF THE INVENTION

The present application relates to lipid assemblies, compositions, and liposomal delivery systems comprising single chain anionic lipids, such as linear alkyl phosphates or phosphonates. Particularly, it involves the use of anionic lysolipids for modifying the surface charge of a cationic lipid composition consisting at least one type of cationic lipid, optionally in combination with one or more neutral lipids and/or one or more anionic lipids. More specifically, the present invention relates to a method of using single chain anionic lipids to switch the positive surface charge of a lipid assembly to a neutral or negative one. Furthermore, the present invention relates to the use of these lipid assembly compositions to facilitate the delivery of a biologically active compound, such as nucleic acids to the target cell.

BACKGROUND OF THE INVENTION

Over the last decades, many biologically active compounds have been developed for the treatment of numerous diseases such as cancer, respiratory and metabolic diseases. Despite the great progress on the way towards the design, specificity and overall development of biologically active compounds, there are still serious issues such as poor bioavailability, safety and limited tissue distribution that hamper their preclinical and clinical applicability. The latter need to be circumvented in order some of these compounds can be safely and successfully applied in the research and clinical field.

Nucleic acid molecules are one major sub class of biologically active compounds and through the progress of the last 30 years, their use in the therapeutic field has evolved from basic science towards applied molecular therapy. Short nucleic acids, such as antisense oligonucleotides, ribozymes, microRNAs, decoys and small interfering RNAs, or long nucleic acids such as plasmids have the ability to regulate RNA. Therefore, the ability to regulate the expression of the target protein in a specific manner, offers unlimited potential for gene therapy, antisense therapy and RNAi therapy among others (Whitehead et al., (2009) Nature Review Drug Discovery 8:129-138). Still, tissue distribution, efficient uptake by the target cell and their trafficking into the cytosol are of major importance for the sequence specific gene regulation. As nucleic acids are large and negatively charged molecules, their passive diffusion through the negatively charged lipophilic cell membrane or their cytosolic internalization by the mechanisms of endocytosis is poor and limits their efficiency. Therefore, the assisted delivery of these nucleic acid molecules is desirable for successful research and therapeutic applications (Behlke, (2006) Molecular Therapy 13:644-670); de Foungerolles et al., (2007) Nature Review Drug Discovery 6:443-453).

Lipid assemblies including liposomes and lipoplexes are one common strategy among non-viral vectors for performing carriage of pharmaceutical substances to target cells. Thus, lipid assemblies have attracted substantial interest as delivery technologies for nucleic acids. In general, there are three main sub types of lipid particles, which have been used over the last decades as delivery systems. Depending on the biophysical properties and more specifically on the surface charge of the lipid membrane, lipid particles are divided into the following main categories: neutral, anionic and cationic lipid particles.

In the past years, only a few neutral and anionic liposomal vectors have been developed. These types of liposomal vehicles are prepared using either neutral lipids, or a combination thereof with anionic lipids. Due to the neutral or anionic charge of the bilayer, these types of lipid membranes demonstrate very low toxicity levels and exhibit relatively long circulation lifetimes, which increases nucleic acid tissue distribution (Landen et al., (2005) Cancer Res. 65:6910-6918 and Halder et. al., (2006) Clin. Cancer Res. 12:4916-4924). Despite these advantages, the relatively high dosages which are needed in order to obtain a pharmacological effect, the low encapsulation efficiencies due to the lack of an electrostatic attraction to the anionic nucleic acids and the poor cellular uptake represent major challenges in these two groups of lipid vehicles (Wang et al., (1987) Proc. Natl. Acad. Sci. 84:7851-7855 and Foged et al., (2006) International Journal of Pharmaceutics 331:160-166).

Compared to the anionic and neutral approaches, cationic liposomal carriers have a positive net surface charge, which facilitates rapid complex formation with negatively charged nucleic acids (Semple et al., (2001) Biochimica et Biophysica Acta 1510:152-166 and Leonetti et al., (2001) Cancer Gene Therapy 8:459-468). In addition, lipid complexes with a positive net charge are readily adsorbed onto the negatively charged cell membrane, leading to a high local nucleic acid concentration at the cell membrane, which supports their intracellular internalization. One example of such vectors is the polycationic liposomes designed by Santel and co-workers, which can mediate delivery of small interfering RNA (siRNA) molecules in endothelial cells in different mouse xenograft tumor models upon intravenous administration (Santel et al., (2006) Gene Therapy 16:1222-1234). Despite encouraging results, it has been observed that inhalable application of these polycationic liposomes evoked inflammation (Gutbier et al., (2010) Pulmonary Pharmacology & Therapeutics 23:334-344). Strong side effects, such as experimental animal death and induction of the immune system were also observed using other polycationic delivery approaches (Bitko et al., (2005) Nature Medicine 11.1:50-55). Although strong cell membrane attraction has advantages, such rapid and non-specific binding of cationic membranes to the anionic cells can also result in high toxicity levels. Aggregate formation with serum components and relatively short circulation lifetimes are additional hurdles to circumvent for the successful application of these carrier systems (Andreakos et al., (2009) Arthritis Rheum. 60:994-1005).

Another interesting strategy of cationic lipid assemblies is the pH sensitive cationic lipid particles of Tekmira pharmaceuticals. These lipid particles have been used successfully for the delivery of siRNAs into the liver and as demonstrated lately the functionality of these vectors depends on the ApoE protein and the use of LDL receptor (Semple et al., (2010) Nature Biotechnology 28:172-176 and Akinc et al., (2010) Molecular Therapy 18:1357-1364). Another example for efficient delivery of siRNA into the liver is the use of permanently charged cationic lipidoids as demonstrated in Akinc et al., (2008) Nature Biotechnology 28:561-569.

However, the dependency of a liposomal delivery system to a specific natural protein or the restricted biodistribution, primarily liver accumulation in the case of cationic lipidoids, narrows the spectrum of in vivo applications.

Thus, the objective of this invention is to provide a method of preparing a drug delivery system, which can transport biologically active compounds, such as nucleic acids or small molecules, proteins and peptides, to the target cells. Another objective of this invention is to provide a mechanism of preparing a carrier, which could combine the advantages of the cationic and anionic liposomal delivery approaches, meaning high encapsulation efficiencies of drug and longer circulation times thus leading to improved tissue distribution and safety. The disclosure also provides compounds and compositions and the use thereof for improving in vitro and in vivo application of biologically active compounds.

SUMMARY OF THE INVENTION

The present application relates to the use of "anionic lysolipids" for the surface modification of cationic assemblies and the creation of an anionic lipid surface charge. In additional embodiments, the modification of cationic assemblies with anionic lysolipids creates a neutral surface charge. The present invention also provides lipid compositions and their use for transfection of cells.

The term "anionic lysolipid" in the scope of the present invention refers to any single chain amphiphilic molecule that is capable of inserting into a membrane and is permanently negatively charged with at least one negative charge at pH values within the range of 4.0 to 8.0. Anionic lysolipids of the present invention comprise a single chain attached to a permanently charged anionic head group. These may be mono- or polyanionic charged single chain amphiphilic molecules.

Anionic lysolipids suitable for the purposes of the present invention comprise, inter alia, compounds from the structural classes of amphiphilic phosphates, phosphonates, sulfates, or sulfonates. Non-limiting examples of anionic lysolipids include (hexadecyl)cetyl phosphate, octadecyl phosphate, hexadecyl phosphonate, 2-hexadecylglycerol biphosphate and monohexadecylpentaerythritol triphosphate.

The term "permanently charged" refers to molecules, lipids, lipid mixtures, lipid assemblies or liposomes that retain their type of charge, either positive or negative over a range of pH value between 4.0 and 8.0.

The use of such single chain lipids in lipid assemblies for transfection of nucleic acids into cells was proposed by the group of Feigner (WO 91/16024). Lyso-phoshatidylcholine (Lyso-PC), a zwitterionic lysolipid with zero net charge, was used in the preparation of a lipid composition in combination with a cationic lipid and a plasmid. The use of Lyso-phoshatidylcholine by the authors aimed at stabilizing the cationic complex and to protect it from any aggregation. This would result in improved transfection activity of the cationic lipoplex. However, in a further publication the authors denied this as they demonstrated that the use of zwitterionic lysolipids does not improve the transfection efficiency of a cationic complex (Felgner et al., (1994) J. Biol. Chem. 269:2550-2561). The use of such single chain lipids for enhanced transfection efficiency of plasmid was additionally disclosed by Meyer, WO 03/052095. The author demonstrated that the use of a formulation comprising zwitterionic lipids, improves the transfer of a polynucleotide into cells compared to free nucleic acid administration. However, in this case, the lack of cationic lipids and thereby of electrostatic interactions between the lipid composition and the nucleic acids could results in poor encapsulation efficiencies. This is a major hurdle for further development of such nucleic acid formulations in the pharmaceutical field.

Another interesting property of these single chain lipids is their ability as single molecules, at values below their respective "critical micelle concentration" (CMC) in water, to integrate into lipid bilayers such as the membrane of cells or liposomes. The insertion of lysolipids in the outer monolayer of a lipid containing membrane can have direct consequences on the bilayer structure and its biophysical properties (Needham and Zhelen, (1995) Annals of Biomedical Engineering 23:287-298).

Taking this property into account, the present invention relates to the use of "anionic lysolipids" such as single chain such as linear alkyl phosphates or phosphonates, for shielding the surface charge of a permanently charged cationic lipid assembly and therefore to convert the surface charge of the lipid assembly from a cationic one to a neutral or even anionic, creating thereby a permanently neutral or anionic charged lipid bilayer.

In more specific aspects of the present invention the permanently charged cationic assemblies comprise at least one type of "cationic lipid", optionally in combination with one or more "neutral lipid(s)" and/or one or more "anionic lipid(s)" in any ratio as long as the surface of the lipid assemblies remains positively charged.

Such permanently charged anionic liposomes of the invention comprise a least one "cationic lipid" and at least one "anionic lysolipid", optionally in combination with one or more "neutral lipid(s)" and/or one or more "anionic lipid(s)", in any ratio as long as the surface of the lipid bilayer remains negatively charged.

The term "cationic lipid" refers to any amphiphilic molecule that is permanently positively charged at pH values within the range of 4.0 to 8.0. Corresponding cationic lipids are characterized by a pKa>9. These lipids usually comprise a diacyl chain or cholesterol attached to a cationic head group such as ammonium, amidinium, guanidinium or pyridinium, or a suitable secondary or tertiary amino group. Non-limiting examples of cationic lipids include DOTAP (1,2-dioleoyl-3-trimethylammonium-propane), TC-Chol (N-trimethylaminoethylcholesterol), DOTMA (1,2-di-O-octadecenyl-3-trimethylammonium propane), DDAB (Dimethyldioctadecylammoniumbromide), DOSPA (Dioleoyloxy-sperminecarboxamido-ethyldimethyl-propanaminiumtrifluoroacetate) and SAINT (Pyridinium amphiphiles analogues).

The term "anionic lipid" refers to any amphiphilic molecule that is permanently negatively charged with at least one negative charge at pH values within the range of 4.0 to 8.0. Corresponding anionic lipids are characterized by at least one pKa<4. These comprise a diacyl chain or cholesterol attached to a head group such as phosphates, phosphonates, sulfates, sulfonates. Non-limiting examples of anionic lipids include DOPS (1,2-dioleoyl-sn-glycero-3-phospho-L-serine), DPPS (1,2-dimyristoyl-sn-glycero-3-phospho-L-serine), DMPA (1,2-dimyristoyl-sn-glycero-3-phosphate), DPPA (1,2-dipalmitoyl-sn-glycero-3-phosphate) and DOPA (1,2-dioleoyl-sn-glycero-3-phosphate).

The term "neutral lipid" refers to cholesterol or any zwitterionic lipid. The term "zwitterionic" refers to any amphiphilic molecule with net zero charge arising from the presence of both, positively and negatively, charged chemical groups at pH values within the range of 4.0 to 8.0. These comprise a diacyl chain attached zwitterionic head group of strong cationic and anionic groups such as phosphatidylethanolamine or phosphatidylcholine. Non-limiting examples of neutral lipids include cholesterol, DMPE (1,2-dimyristoyl-sn-glycero-3-phosphate-phosphoethanolamine), DOPE (1,2-dioleoyl-sn-glycero-3-phosphoethanolamine), POPC (1-palmitoyl-2-oleoyl-sn-glycero-3-phosphocholine), and DMPC (1,2-dimyristoyl-sn-glycero-3-phosphocholine).

In a further related embodiment, lipid assembly of the present invention may comprise additional components such as hydrophilic polymers chains or ligands. Incorporation of hydrophilic polymers chains such as PEG-lipids to a lipid mixture could further enhance the stability of the particle during formation with nucleic acids and reduce aggregation upon storage. However, increased amounts of PEG-lipids in a lipid particle could additionally result in loss of transfection activity of the particle. The above mentioned properties are dependent on the length and saturation of lipid chain and the size of the head group. Typically, in the present invention, without being limited to, the amount of PEG-lipids in a lipid composition may reach concentrations up to 5 mole %. Non-limiting examples of pegylated lipids include C8-750PEG, C16-750PEG, C8-2000PEG, C16-2000PEG, MPEG-750-DMPE, MPEG-750-DLPE, MPEG-750-DSPE, MPEG-2000-DMPE, MPEG-2000-DLPE and MPEG-2000-DSPE.

In related embodiments of the present invention, design of the lipid assemblies may employ ligand molecules exposed on the lipid surface. Incorporation of targeting-ligands in a lipid assembly would enhance cell/tissue specificity and intracellular internalisation of the lipid assembly resulting in increased drug concentrations within the cell.

In particular embodiments, the lipid assemblies of the present invention comprise biological-active agents. In more specific embodiments, and without being limited to, the biological active agent are nucleic acids containing less than 100 nucleotides or chemically modified analogs thereof, named as oligonucleotides. Non-limiting examples of oligonucleotides are provided below:

Short interfering RNAs (siRNA) are double-stranded RNA molecules and are designed to target the mRNA sequence through the RNA interference (RNAi) pathway (Fire et al., (1998) Nature 391:806-11) in specific manner.

Antisense oligonucleotides are short single-stranded nucleotide sequences. They bind to the target messenger RNA sequence through Watson-Crick base pairing resulting in inhibition of the protein translation process.

Antagomirs (anti-miR) are single-stranded oligonucleotides complementary to specific miRNAs (microRNAs). Antagomirs are used to silence endogenous microRNAs and block their biological activity.

MiR-mimics are double-stranded oligonucleotides and are designed to functionally mimic endogenous microRNAs in more specific fashion.

Decoy oligonucleotides are double-stranded DNA molecules and can modulate target expression through binding to DNA-binding transcriptions factors.

Ribozymes (ribonucleic acid enzyme) are single-stranded molecules with an enzymatic catalytic activity. Catalytic efficient ribozymes, inter alia, catalyze the cleavage of phosphodiester bonds in other RNAs.

DNAzymes (DNA enzymes) are as Ribozymes single-stranded catalytically active DNA molecules. DNAzymes are characterized by their capability to bind and cleave RNA molecules in a site-specific manner.

In some embodiments, the present invention includes lipid assemblies for the transfection of a cell in vitro, ex vivo and in vivo. The liposomes and compositions of the present disclosure may be used for the delivery of biologically active compounds in variety of tissues. Particularly, in certain embodiment, the present invention discloses lipid particles for siRNA delivery in the lung epithelium. The respiratory epithelium is a site of particular interest for oligonucleotide-based therapies and related delivery technologies.

The respiratory epithelium lining the respiratory tract moistens and protects the airways, functions as a barrier to potential pathogens and foreign particles, and controls protective immune responses in the airways. However, the respiratory epithelium can also contribute to the development of respiratory diseases, such as asthma, chronic obstructive pulmonary disease (COPD), cystic fibrosis, and respiratory infection. Therefore, various approaches are being considered for controlling inappropriate responses of the respiratory epithelium and include administration of inhalable therapeutics where the biologically active substance is usually a small molecule (e.g. a corticosteroid or β-adrenergic receptor blocker). Inhalable administration of oligonucleotide-based therapeutics, although desirable, has been hampered by the inefficient delivery of the relatively large size of the active compound (e.g. siRNA or antisense oligonucleotides) and the difficulty of restricting targeting to the bronchial or alveolar epithelium.

BRIEF DESCRIPTION OF THE FIGURES

FIG. 2 shows fluorescence microscopy images of lung tissues of mice after intratracheal administration of saline, free siRNA (Cy5 labelled non-target siRNA) and lipid particles (Formulation I and II) of the present invention comprising Cy5 labelled non-target siRNA according to Example 7 of the present invention.

FIG. 3 shows fluorescence microscopy images of lung tissues of mice after intranasal administration of saline, free siRNA (Cy5 labelled non-target siRNA) and lipid particles (Formulation I and II) of the present invention comprising Cy5 labelled non-target siRNA according to Example 7 of the present invention.

FIG. 7 shows ISG15 and OAS1 mRNA levels in the lungs of mice measured 48 h after treatment with liposomes of the present invention containing siRNA targeting Ecadherin and saline according to Example 9 of the present invention.

FIG. 8 shows FACS analysis of CD45$^+$ cells (Immune cells) and CD11b$^+$ Gr1$^+$ of CD45$^+$ cells (Neutrophils) in the lungs of mice measured 48 h after treatment with the lipid particles of the present invention containing siRNA targeting Ecadherin (Formulation A), control siRNA (Formulations B), empty lipid particles (Formulation C) and saline according to Example 9 of the present invention.

DETAILED DESCRIPTION OF THE INVENTION

Figure 1:
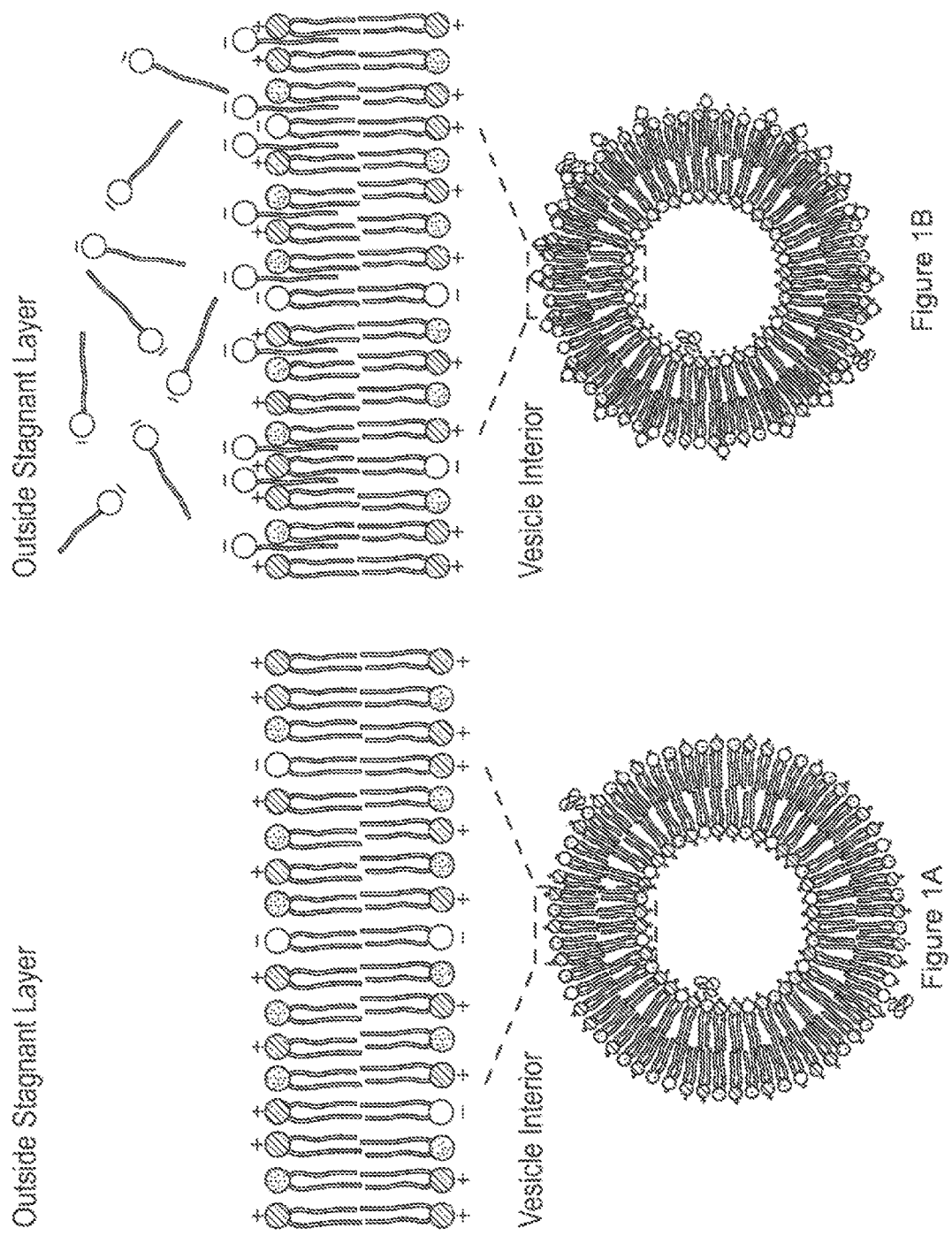
FIG. 1A shows a scheme of a liposome wherein the lipid bilayer comprises one type of anionic lipid, one type of cationic lipid, one type of neutral lipid, wherein the positive charges from the cationic lipid exceed the negative charges from the anionic lipid.
FIG. 1B shows a scheme of a liposome of FIG. 1A wherein the outer layer of the lipid bilayer is modified by insertion of the anionic lysolipid in a sufficient concentration to provide the liposome with a permanent anionic surface charge according to the present invention.

The invention is particularly represented by the following embodiments:

1. A lipid assembly comprising at least one lipid bilayer, wherein said lipid bilayer comprises at least one type of cationic lipid, and optionally at least one type of neutral lipid, characterized in that the outermost layer of the lipid bilayer of the lipid assembly further comprises at least one type of anionic lysolipid, wherein said anionic lysolipid is negatively charged at a pH within the range of 4 to 8, and wherein the lysolipid is present in a sufficient concentration to provide the lipid assembly with an anionic surface charge at a pH within the range of 4 to 8, or to provide the lipid assembly with a net zero surface charge at a pH within the range of 4 to 8.
2. A lipid assembly according to item 1, wherein the lipid bilayer comprises at least one type of anionic lipid, at least one type of cationic lipid, and optionally at least one type of neutral lipid, wherein the positive charges from the at least one type of cationic lipid exceed the negative charges from the at least one type of anionic lipid, characterized in that the outermost layer of the lipid bilayer of the lipid assembly further comprises at least one type of anionic lysolipid, wherein said anionic lysolipid is negatively charged at a pH within the range of 4 to 8, and wherein the lysolipid is present in a sufficient concentration to provide the lipid assembly with an anionic surface charge at a pH within the range of 4 to 8, or to provide the lipid assembly with a net zero surface charge at a pH within the range of 4 to 8.
3. The lipid assembly according to item 1 or 2, wherein the at least one type of anionic lysolipid is present in a sufficient concentration to provide the lipid assembly with a net zero surface charge at a pH within the range of 4 to 8.
4. The lipid assembly according to item 1 or 2, wherein the at least one type of anionic lysolipid is present in a sufficient concentration to provide the lipid assembly an anionic surface charge at a pH within the range of 4 to 8.
5. The lipid assembly according to any one of items 1-4, wherein the at least one type of anionic lysolipid is capable to insert into a lipid bilayer.
6. The lipid assembly according to any one of items 1-4, wherein the at least one type of anionic lysolipid is an amphiphilic molecule consisting of a polar head group and a single hydrocarbon chain.
7. The lipid assembly according to any one of items 1-4, wherein the at least one type of anionic lysolipid is selected from the group consisting of phosphates, phosphonates, sulfates, or sulfonates.
8. The lipid assembly according to any one of items 1-4, wherein the at least one type of anionic lysolipid is mono anionic or poly anionic at a pH within the range of 4 to 8.
9. The lipid assembly according to any one of the preceding items, wherein the at least one type of anionic lysolipid is selected from the group consisting of formula (I) to formula (VI)

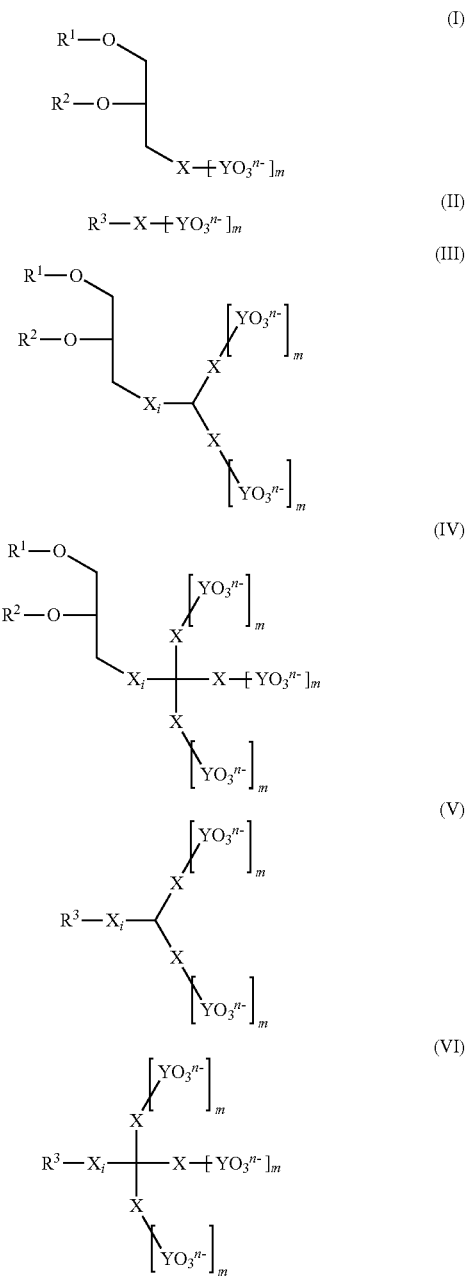

wherein:
X is absent or is selected from a group consisting of —R$^4$—, —R$^4$—O—, —O—R$^4$—, —R$^4$—NH—, —NH—R$^4$—, —R$^4$—C(O)—NH—, —C(O)—NH—R$^4$—, —R$^4$—C(O)—O—, —C(O)—O—R$^4$—, —R$^4$—O—C(O)—, —O—C(O)—R$^4$—, —R$^4$—O—C(O)—NH, —O—C(O)—NH—R$^4$—, —R$^4$—NH—C(O)—O—, —NH—C(O)—O—R$^4$—, —(YO$_3^{n-}$)$_{1-5}$—R$^4$— or —O—(YO$_3^{n-}$)$_{1-5}$—R$^4$—;

$X_i$ is absent or is selected from a group consisting of —$R^4$—, —$R^4$—O—, —O—$R^4$—, —$R^4$—NH—, —NH—$R^4$—, —$R^4$—C(O)—NH—, —C(O)—NH—$R^4$—, —$R^4$—C(O)—O—, —C(O)—O—$R^4$—, —$R^4$—O—C(O)—, —O—C(O)—$R^4$—, —$R^4$—O—C(O)—NH, —O—C(O)—NH—$R^4$—, —$R^4$—NH—C(O)—O—, —NH—C(O)—O—$R^4$—, —(YO$_3{}^{n-}$)$_{1-5}$—$R^4$— or —O—(YO$_3{}^{n-}$)$_{1-5}$—$R^4$—;

Y is P or S;

n is 1 or 2;

m is 1, 2, 3, 4, or 5;

$R^1$ and $R^2$ are selected from hydrogen, $C_5$-$C_{30}$ alkylcarbonyl, $C_5$-$C_{30}$ alkenylcarbonyl, $C_5$-$C_{30}$ alkynylcarbonyl, with the proviso that one of the groups $R^1$, $R^2$ is hydrogen, while the other group is not hydrogen;

$R^3$ is selected from $C_5$-$C_{30}$ alkyl, $C_5$-$C_{30}$ alkenyl, or $C_5$-$C_{30}$ alkynyl;

$R^4$ is absent or is selected from $C_1$-$C_{30}$ alkylene, $C_2$-$C_{30}$ alkenylene, or $C_2$-$C_{30}$ alkynylene.

10. The lipid assembly according to item 9, wherein the at least one type of anionic lysolipid is selected from the group consisting of formula (I), wherein X is O, Y is P, m is 1, and n is 2.

11. The lipid assembly according to item 9, wherein the at least one type of anionic lysolipid is selected from the group consisting of formula (II), wherein X is O, Y is P, m is 1 and n is 2.

12. The lipid assembly according to item 9, wherein the at least one type of anionic lysolipid is selected from the group consisting of formula (II), wherein X is absent, Y is P, m is 1, and n is 2.

13. The lipid assembly according to item 9, wherein the at least one type of anionic lysolipid is selected from the group consisting of formula (II), wherein X is O, Y is S, m is 1, and n is 1.

14. The lipid assembly according to item 9, wherein the at least one type of anionic lysolipid is selected from the group consisting of formula (II), wherein X is absent, Y is S, m is 1, and n is 1.

15. The lipid assembly according to item 9, wherein the at least one type of anionic lysolipid is selected from the group consisting of formula (III), wherein $X_i$ is absent, X is O, Y is P, m is 1 and n is 2.

16. The lipid assembly according to item 9, wherein the at least one type of anionic lysolipid is selected from the group consisting of formula (IV), wherein $X_i$ is absent, X is O, Y is P, m is 1 and n is 2.

17. The lipid assembly according to item 9, wherein the at least one type of anionic lysolipid is selected from the group consisting of formula (V), wherein $X_i$ is O, X is O, Y is P, m is 1 and n is 2.

18. The lipid assembly according to item 9, wherein the at least one type of anionic lysolipid is selected from the group consisting of formula (V), wherein $X_i$ is absent, X is O, Y is P, m is 1 and n is 2.

19. The lipid assembly according to item 9, wherein the at least one type of anionic lysolipid is selected from the group consisting of formula (V), wherein $X_i$ is O, X is absent, Y is P, m is 1 and n is 2.

20. The lipid assembly according to item 9, wherein the at least one type of anionic lysolipid is selected from the group consisting of formula (V), wherein $X_i$ is absent, X is absent, Y is P, m is 1, and n is 2.

21. The lipid assembly according to item 9, wherein the at least one type of anionic lysolipid is selected from the group consisting of formula (V), wherein $X_i$ is O, X is O, Y is S, m is 1 and n is 1.

22. The lipid assembly according to item 9, wherein the at least one type of anionic lysolipid is selected from the group consisting of formula (V), wherein $X_i$ is absent, X is O, Y is S, m is 1, and n is 1.

23. The lipid assembly according to item 9, wherein the at least one type of anionic lysolipid is selected from the group consisting of formula (V), wherein $X_i$ is O, X is absent, Y is S, m is 1 and n is 1.

24. The lipid assembly according to item 9, wherein the at least one type of anionic lysolipid is selected from the group consisting of formula (V), wherein $X_i$ is absent, X is absent, Y is S, m is 1, and n is 1.

25. The lipid assembly according to item 9, wherein the at least one type of anionic lysolipid is selected from the group consisting of formula (VI), wherein $X_i$ is O, X is O, Y is P, m is 1 and n is 2.

26. The lipid assembly according to item 9, wherein the at least one type of anionic lysolipid is selected from the group consisting of formula (VI), wherein $X_i$ is absent, X is O, Y is P, m is 1 and n is 2.

27. The lipid assembly according to item 9, wherein the at least one type of anionic lysolipid is selected from the group consisting of formula (VI), wherein $X_i$ is O, X is absent, Y is P, m is 1, and n is 2.

28. The lipid assembly according to item 9, wherein the at least one type of anionic lysolipid is selected from the group consisting of formula (VI), wherein $X_i$ is absent, X is absent, Y is P, m is 1, and n is 2.

29. The lipid assembly according to item 9, wherein the at least one type of anionic lysolipid is selected from the group consisting of formula (VI), wherein $X_i$ is O, X is O, Y is S, m is 1, and n is 1.

30. The lipid assembly according to item 9, wherein the at least one type of anionic lysolipid is selected from the group consisting of formula (VI), wherein $X_i$ is absent, X is O, Y is S, m is 1, and n is 1.

31. The lipid assembly according to item 9, wherein the at least one type of anionic lysolipid is selected from the group consisting of formula (VI), wherein $X_i$ is O, X is absent, Y is S, m is 1, and n is 1.

32. The lipid assembly according to item 9, wherein the at least one type of anionic lysolipid is selected from the group consisting of formula (VI), wherein $X_i$ is absent, X is absent, Y is S, m is 1, and n is 1.

33. The lipid assembly according to any one of items 9 to 32, wherein the alkyl, alkenyl, or alkynyl groups in the substituents $R^1$, $R^2$ or $R^3$ are linear alkyl, alkenyl, or alkynyl groups.

34. The lipid assembly according to any one of the items 1 to 9, wherein the anionic lysolipid is selected from the group of dodecyl phosphate, tetradecyl phosphate (hexadecyl)cetyl phosphate, octadecyl phosphate, decyl phosphonate, hexadecyl phosphonate, octadecyl phosphonate, 2-hexadecylglycerol biphosphate and monohexadecylpentaerythritol triphosphate.

35. The lipid assembly according to any one of the preceding items, wherein
   (a) the at least one type of cationic lipid has a pKα of more than 9 or at least one positive charge at the pH range of 4 to 8.
   (b) the at least one type of anionic lipid pKα of less than 4 or at least one negative charge at the pH range of 4 to 8.

36. The lipid assembly according to any one of the preceding items, wherein
   (a) the at least one type of cationic lipid is selected from the group consisting of DMTAP (1,2-dimyristoyl-3- trimethylammonium-propane), DPTAP (1,2-dipalmitoyl-3-trimethylammonium-propane), POTAP (Palmitoyloleoyl-3-Trimethylammonium-Propane), DMRIE (N-[1(2,3-dimyristyloxy)propyl]-N,N-dimethyl-N-(2-hydroxyethyl) ammonium bromide), DOTAP (1,2-dioleoyl-3-trimethylammonium-propane), DOGS (dioctadecylamidoglycylspermine), TC-Chol (N-trimethylaminoethylcholesterol), DOTMA (1,2-di-O-octadecenyl-3-trimethylammonium propane), DHMHAC (N,N-di-n-hexadecyl-N,methyl, N-(2-hydroxyethyl)ammonium chloride), DHDEAB (N,N-di-n-hexadecyl-N,N-dihydroxyethylammonium bromide), DDAB (Dimethyldioctadecylammoniumbromide), DORI ((N-[1-(2,3-Dioleoyloxy)propyl]-(N,N-dimethyl,N-hydroxyethyl]ammonium), DOP6P (1,2-Dioleoyl-sn-glycero-3-N-pryridinium), DOSPER (1,3-dioleoyloxy-2-(6-carboxy-spermyl)-propylamid), Chol-Betaine (Cholesteryl-oxycarbonylmethyl-trimethyl-ammonium), DOSPA (Dioleoyloxy-sperminecarboxamido-ethyldimethyl-propanaminiumtrifluoroacetate), SAINT (Pyridinium amphiphiles analogues) and GL-67 ([Cholest-5-en-3-ol(3b)-3-[(3-aminopropyl)[4-[(3-aminopropyl)amino]butyl]carbamate]).

(b) the at least one type of anionic lipid is selected from the group consisting of cholesterol phosphate, cholesterol sulfate, DMPS (1,2-dimyristoyl-sn-glycero-3-phospho-L-serine), DPPS (1,2-dipalmitoyl-sn-glycero-3-phospho-L-serine), DOPS (1,2-dioleoyl-sn-glycero-3-phospho-L-serine), POPS (1-palmitoyl-2-oleoyl-sn-glycero-3-phospho-L-serine), DLPA (1,2-dilauroyl-sn-glycero-3-phosphate), DMPA (1,2-dimyristoyl-sn-glycero-3-phosphate), DPPA (1,2-dipalmitoyl-sn-glycero-3-phosphate), DOPA (1,2-dioleoyl-sn-glycero-3-phosphate), 18:2 PA (1,2-dilinolenoyl-sn-glycero-3-phosphate), DSPA (1,2-D-sn-glycero-3-phosphate), POPA (1-palmitoyl-2-oleoyl-sn-glycero-3-phosphate), SOPA (1-stearoyl-2-oleoyl-sn-glycero-3-phosphate) and DCP (dicetyl phosphate).

(c) the at least one type of neutral or zwitterionic lipid is independently selected from the group consisting of Cholesterol, DLPE (1,2-dilauroyl-sn-glycero-3-phosphoethanolamine), DMPE (1,2-dimyristoyl-sn-glycero-3-phosphate-phosphoethanolamine), DPPE (1,2-dipalmitoleoyl-sn-glycero-3-phosphoethanolamine), DOPE (1,2-dioleoyl-sn-glycero-3-phosphoethanolamine), POPE (1-palmitoyl-2-oleoyl-sn-glycero-3-phosphoethanolamine), DLinPE (1,2-dilinoleoyl-sn-glycero-3-phosphoethanolamine), DSPE (1,2-D-sn-glycero-3-phosphoethanolamine), POPC (1-palmitoyl-2-oleoyl-sn-glycero-3-phosphocholine), DOPC (1,2-dioleoyl-sn-glycero-3-phosphocholine), DMPC (1,2-dimyristoyl-sn-glycero-3-phosphocholine), phosphatidylcholine, phosphatidylethanolamine, sphingomyeline, or mixtures thereof.

37. The lipid assembly according to any of the preceding items, further comprising polymer-lipid conjugates or polymeric lipids.
38. The lipid assembly according to item 37, wherein the polymer-lipid conjugates or polymeric lipids are selected from the group consisting of monomethoxypolyethyleneglycol (mPEG) or polyethyleneglycol (PEG) based lipids.
39. The lipid assembly according to item 38, wherein the PEG is conjugated to a ceramide lipid, such as C8-ceramide (N-octanoyl-ceramide), C14-ceramide (N-myristoyl-D-erythro-sphingosine), C16-ceramide (N-palmitoyl-D-erythro-sphingosine) and C20-ceramide (N-arachidoyl-D-erythro-sphingosine).
40. The lipid assembly according to item 38, wherein the PEG is conjugated to lipids such as DOPE; DLPE, DDPE, DLinPE, DMPE, DPPE and DSPE.
41. The lipid assembly according to items 37 to 40, wherein the molecular weight of the PEG part of the polymer-lipid conjugate is about 350 Da, or about 550 Da, or about 750 Da, or about 1000 Da, or about 1500 Da, or about 2000 Da, or about 3000 Da, or about 3500 Da, or about 5000 Da.
42. The lipid assembly according to any one of items 37 to 41, wherein the pegylated lipid is selected from the group consisting of C8-750PEG, C16-750PEG, C8-2000PEG, C16-2000PEG, MPEG-750-DMPE, MPEG-750-DLPE, MPEG-750-DSPE, MPEG-2000-DMPE, MPEG-2000-DLPE and MPEG-2000-DSPE.
43. The lipid assembly according to any of the preceding items, wherein the lipid assembly is modified with a ligand for specific targeting of a cell/tissue, and wherein said ligand is admixed with the composition compounds or conjugated to a lipid of the composition.
44. The lipid assembly according to item 43, wherein the ligand for specific targeting of a cell/tissue is selected from the group consisting of a protein, a peptide, a small molecule, an antibody, an antigen, an allergen, a carbohydrate, a nucleic acid, or a lectin.
45. The lipid assembly according to any of the preceding items, wherein the lipid components may assemble to a lamella vesicle, a lipid particle, a liposome, a carrier, a lipoplex or a structure with an agues interior.
46. The lipid assembly according to item 45, wherein the lipid assembly is a liposome.
47. The liposome according to item 46, wherein the liposome is a monolammellar liposome.
48. The liposome according to item 46, wherein the liposome is a multilamellar liposome.
49. The liposome according to any of the items 46-48, wherein the liposome has a size from about 1 nm to about 1000 nm, or from about 200 nm and about 400 nm, or from about 50 nm and 200 nm.
50. The lipid assembly according to any of the preceding items, wherein the lipid assembly comprises one or more biologically active agents selected from the group of nucleic acids, peptides, proteins, or small molecules.
51. The lipid assembly according to item 50, wherein the biological active agent is loaded or complexated or encapsulated within the lipid assembly or/and is bound to the inner or outer lipid layer of the lipid assembly or/and is present between the layers of the lipid assembly.
52. The lipid assembly according to item 50, wherein the nucleic acid is a DNA molecule or an RNA molecule.
53. The lipid assembly according to item 50, wherein the nucleic acid is an oligonucleotide.
54. The lipid assembly according to item 53, wherein the oligonucleotide is a short interfering RNA (siRNA), an antisense oligonucleotide, a double stranded RNA (dsRNA), a short hairpin RNA (shRNA), a decoy oligonucleotide, a ribozyme, DNAzyme, an aptamer, a microRNA, an anti-miR (antagomir) or a miR-mimic.
55. The lipid assembly according to any one of items 50 to 54, wherein the nucleic acid comprises modified nucleosides.
56. The lipid assembly according to item 55, wherein the modified nucleic acids are selected from the group consisting of DNA or RNA modified nucleotides, locked nucleic acids (LNA), 2'-fluoro nucleotides, 2'-O-methyl (2' OMe) nucleotides, 2'-O-methoxyethyl (MoE) nucleotides, peptide nucleic acids (PNAs), phosphorothioate nucleotides, morpholinophosphoroamidates (MFs) or unlocked nucleic acids (UNA).

57. The lipid assembly according to any of the preceding items for use in diagnosis or therapy.
58. The lipid assembly according to any of the preceding items for use in the treatment of diseases such as respiratory, cardiovascular, infectious, metabolic, inflammatory, autoimmune, gastrointestinal and neurodegenerative diseases, and cancer.
59. The lipid assembly according to any one of the preceding items for the delivery of biologically active agents to the epithelial surface of mucous membranes.
60. A pharmaceutical formulation comprising the lipid assembly according to any one of the preceding items and one or more pharmaceutically acceptable excipient(s).
61. A method for the preparation of a lipid assembly, characterized by the following steps:
    (a) preparing a lipid assembly comprising at least one lipid bilayer, wherein said lipid bilayer comprises at least one type of cationic lipid, and optionally at least one type of neutral lipid, and further optionally at least one type of anionic lipid;
    (b) treating the lipid assembly from step (a) with a solution of at least one type of anionic lysolipid as defined in item 1, and
    (c) optionally isolating the lipid assembly obtained in step (b).
62. A method for the preparation of a lipid assembly, characterized by the following steps:
    (a) preparing a liposome comprising at least one lipid bilayer, wherein said lipid bilayer comprises at least one type of anionic lipid, at least one type of cationic lipid, and optionally at least one type of neutral lipid, wherein the at least one type of cationic lipid is present in excess to the at least one type of anionic lipid;
    (b) treating the lipid assembly from step (a) with a solution of at least one type of anionic lysolipid as defined in item 1, and
    (c) optionally isolating the lipid assembly obtained in step (b).
63. The method according to item 61 or 62, wherein the amount of the at least one type of anionic lysolipid in step (b) is sufficient to provide the lipid assembly with a permanent negative surface charge at a pH within the range of 4 to 8.
64. The method according to item 61 or 62, wherein the amount of the at least one type of anionic lysolipid in step (b) is sufficient to provide the lipid assembly with a net zero surface charge at a pH within the range of 4 to 8.
65. The method according to any one of items 61 to 64, wherein the concentration of the solution of the at least one type of anionic lysolipid in step (b) is below the critical micelle concentration (CMC) for the at least one type of lysolipid.
66. The method according to any one of items 61 to 65, wherein the at least one type of anionic lysolipid in step (b) is capable to insert into a lipid bilayer.
67. The method according to any one of items 61 to 66, wherein the at least one type of anionic lysolipid in step (b) is an amphiphilic molecule consisting of a polar head group and a single hydrocarbon chain.
68. The method according to any one of items 61 to 67, wherein the at least one type of anionic lysolipid in step (b) is selected from the group consisting of phosphates, phosphonates, sulfates, or sulfonates.
69. The method according to any one of items 61 to 68, wherein the at least one type of anionic lysolipid in step (b) is mono anionic or poly anionic at a pH within the range of 4 to 8.
70. The method according to any one of items 61 to 69, wherein the at least one type of anionic lysolipid in step (b) is selected from the group consisting of formula (I) or formula (II)

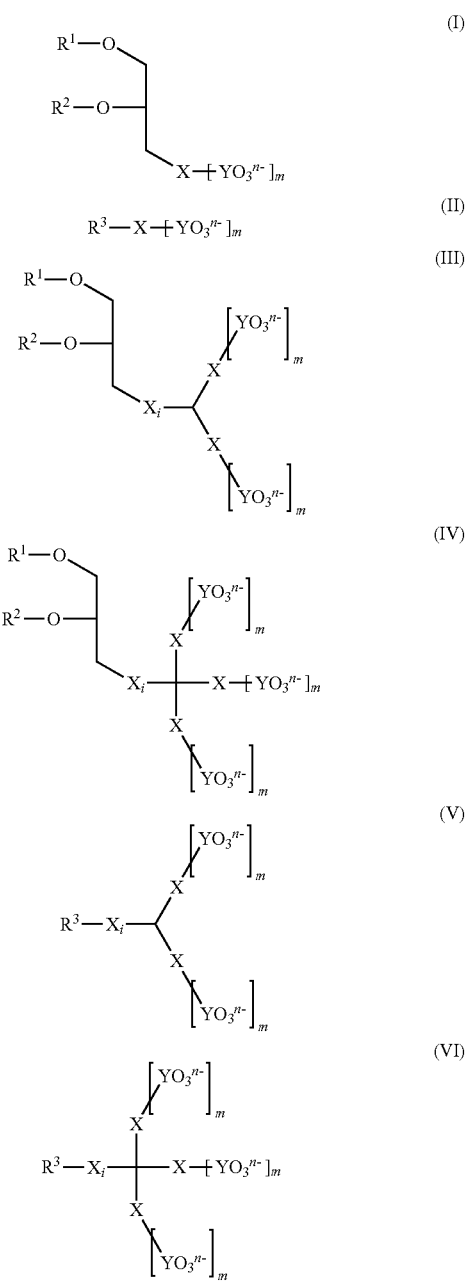

wherein:
X is absent or is selected from a group consisting of —R$^4$—, —R$^4$—O—, —O—R$^4$—, —R$^4$—NH—, —NH—R$^4$—, —R$^4$—C(O)—NH—, —C(O)—NH—R$^4$—, —R$^4$—C(O)—O—, —C(O)—O—R$^4$—, —R$^4$—O—C(O)—, —O—C(O)—R$^4$—, —R$^4$—O—C(O)—NH, —O—C(O)—NH—R$^4$—, —R$^4$—NH—C (O)—O—, —NH—C(O)—O—R⁴—, —(YO₃ⁿ⁻)₁₋₅—R⁴— or —O—(YO₃ⁿ⁻)₁₋₅—R⁴—;

X$_i$ is absent or is selected from a group consisting of —R⁴—, —R⁴—O—, —O—R⁴—, —R⁴—NH—, —NH—R⁴—, —R⁴—C(O)—NH—, —C(O)—NH—R⁴—, —R⁴—C(O)—O—, —C(O)—O—R⁴—, —R⁴—O—C(O)—, —O—C(O)—R⁴—, —R⁴—O—C(O)—NH, —O—C(O)—NH—R⁴—, —R⁴—NH—C(O)—O—, —NH—C(O)—O—R⁴—, —(YO₃ⁿ⁻)₁₋₅—R⁴— or —O—(YO₃ⁿ⁻)₁₋₅—R⁴—;

Y is P or S;
n is 1 or 2;
m is 1, 2, 3, 4, or 5;
R¹ and R² are selected from hydrogen, C₅-C₃₀ alkylcarbonyl, C₅-C₃₀ alkenylcarbonyl, C₅-C₃₀ alkynylcarbonyl, with the proviso that one of the groups R¹, R² is hydrogen, while the other group is not hydrogen;
R³ is selected from C₅-C₃₀ alkyl, C₅-C₃₀ alkenyl, or C₅-C₃₀ alkynyl;
R⁴ is absent or is selected from C1-C₃₀ alkylene, C₂-C₃₀ alkenylene, or C₂-C₃₀ alkynylene.

71. The method according to any one of items 61 to 70, further comprising the step of formulating the lipid assembly obtained therein into a pharmaceutical composition.
72. The method according to any one of items 61 to 71, wherein the lipid assembly prepared in step a) comprises at least one biologically active agent selected from the group of nucleic acids, peptides, proteins, or small molecules.
73. The method according to any one of items 61 to 72, wherein the biological active agent is loaded, complexated, encapsulated within the lipid assembly or/and is bound to the inner or outer lipid layer of the lipid assembly or/and is present between the layers of the lipid assembly.
74. The method according to item 72 or 73, wherein the nucleic acid is an oligonucleotide.
75. The method according to item 74, wherein the oligonucleotide is a short interfering RNA (siRNA), an antisense oligonucleotide, a double stranded RNA (dsRNA), a short hairpin RNA (shRNA), a decoy oligonucleotide, a ribozyme, DNAzyme, an aptamer, a microRNA, an antimiR (antagomir) or a miR-mimic.
76. The method according to any one of items 72 to 75, wherein the nucleic acid comprises modified nucleosides.
77. The method according to item 76, wherein the modified nucleic acids are selected from the group consisting of DNA or RNA modified nucleotides, locked nucleic acids (LNA), 2'-fluoro nucleotides, 2'-O-methyl (2' OMe) nucleotides, 2'-O-methyxyethyl (MoE) nucleotides, peptide nucleic acids (PNAs), phosphorothioate nucleotides, morpholinophosphoroamidates (MFs) or unlocked nucleic acids (UNA).
78. The lipid assembly obtained by the method of any one of items 61 to 77, wherein the lipid assembly is a liposome.
79. The liposome according to item 78 for use in diagnosis or therapy.
80. The liposome according to item 78 for use in treatment of diseases such as respiratory, cardiovascular, infectious, metabolic, inflammatory, autoimmune, gastrointestinal and neurodegenerative diseases, and cancer.
81. The liposome according to item 78 for the delivery of biologically active agents to the epithelial surface of mucous membranes.

EXAMPLES

The present invention is illustrated by the following examples. However, the examples should in no way be construed as limiting the scope of the invention.

I. Example 1—Creating Negatively Charged Liposomes Mathematical Calculations

The present invention discloses the use of anionic single chain lipids, anionic lysolipids, for modifying positively charged bilayers comprising mixtures of cationic and anionic lipids, both being charged at physiological conditions, resulting in an anionic surface charge. To further illustrate the teachings of this invention, mathematical calculations were used to provide herewith an example of modifying cationic assemblies with anionic lysolipids.

The absolute fraction of charges in a lipid assembly, comprising cationic and anionic amphiphilic molecules, depends on the pKα of both charged species and is a function of the pH of the medium. Cationic lipids characterized by a pKα greater than 9, exhibit a single positive charge (+1) at pH values lower than 9. Anionic lipids characterized by pKα values of ~3.0 and ~8.0, exhibits a single negative charge (−1) at pH values around 4, where at pH values between 7 and 8 exhibit a double negative charge (−2). Over the entire range of pH the free charges $X_{|CHARGES|}$ of a certain lipid composition can be expressed as:

$$X_{|CHARGES|} = \left(\frac{1}{2}Z_{CAT}\frac{(yi-1)+10^{pK-pH}}{1+10^{pK-pH}}\right) + \left(\frac{1}{2}Z_{AN}\frac{(yi-1)+10^{pK-pH}}{1+10^{pK-pH}}\right) \quad \text{(Equation I)}$$

where Z is the molar fraction of the appropriate species and depends on the pKα of the lipid and the pH of the medium; CAT and AN are the uncharged cationic and anionic species; yi is the absolute charge of the individual groups below their pKa; ½, the charge of a given lipid bilayer is calculated only for the outer layer of the membrane.

As an example, a cationic lipid assembly comprises a molar composition of 45 mole DOTAP, a cationic lipid with an ammonium head group, 15 mole DOPA, an anionic lipid with a phosphatic acid head group, and 40 mole of the neutral lipid cholesterol. The surface charge of this lipid mixture can be calculated from the sum of charged species only in the outer layer of the lipid bilayer; which is 22.5 mole DOTAP and 7.5 mole DOPA. Cholesterol has no net charge; thus is not taken into account. The absolute ratio of cationic to anion charges (C:A) is 3 (22.5/7.5) resulting in an excess of 15 mole cationic lipid over the anionic lipid. At low pH values the phosphate group from DOPA exhibits a single negative charge (−1) which results to 15 mole remaining positive charges. Where at physiological or high pH values the phosphate group exhibits a double negative charge (−2) and the remaining positive charges are a result of the 7.5 mole DOTAP. Over the entire range of pH the surface charge of this certain lipid composition is positive.

The preformed cationic membrane described herein enables the loading of high amounts of nucleic acids into the liposomes. However, upon in vivo administration the positive surface charge of these liposomes can be of a disadvantage, leading to aggregation, instability and short circulation times.

Thus, an object of the present invention is to provide lipid assemblies or lipid mixtures or liposomes capable of circumventing these challenges. Therefore these preformed cationic liposomes are finally shielded with anionic lysolipids. The single chain hydrophobic part of the lysolipid allows the insertion of the lipid into the preformed lipid membrane. In that event, as an example, a separate addition of 20 mole hexadecyl phosphate in the preformed cationic lipid bilayer described herein will result to insertion of this lipid in the outer surface of the lipid bilayer and in an excess of the anionic charges over the positive ones. The new lipid bilayer will be then a result of mixing 22.5 mole DOTAP and 7.5 mole DOPA modified with 20 mole hexadecyl phosphate. The sum of DOPA and lysolipid, both characterized by the anionic charges of the phosphate head group, will prevail over DOTAP at low and physiological/high pH values, thereby creating a negative charged liposome.

The remaining free charges $X_{|CHARGES|}$ of the final charged lipid species can now be expressed as:

$$X_{|CHARGES|} = \left(\frac{1}{2}Z_{CAT}\frac{(yi-1)+10^{pK-pH}}{1+10^{pK-pH}}\right) + \left(\frac{1}{2}Z_{AN}\frac{(yi-1)+10^{pK-pH}}{1+10^{pK-pH}}\right) + \left(Z_{ANL}\frac{(yi-1)+10^{pK-pH}}{1+10^{pK-pH}}\right)$$ (Equation II)

where $Z_{ANL}$ is the molar fraction of the anionic lysolipid in the outer layer of the lipid bilayer.

The beneficial effect of shielding cationic lipid particles with single chain anionic lipids and therefore creating an anionic character is that it prevents carrier leakage and inhibits the ability of the vector to form uncontrolled aggregates with serum components. This could result in more safe/tolerated liposomes with prolonged circulation lifetimes resulting in enhanced delivery of biologically active compounds to the target tissues.

The lipid composition analysed above is illustrating the teachings of the present invention, without limiting it to the specific example. It is possible to change the charged lipids as well as the neutral lipids and the anionic lysolipids used in this specific composition. Additional changes could also be made regarding the ratio between the charged lipids and the absolute amount of all lipids used in this example. The addition of extra components such as PEG-lipids or ligands is not limited in the present invention.

II. Example 2—Preparation of Liposomes

Individual lipid stock solutions were prepared by dissolving the lipids in alcoholic solutions such as isopropanol or ethanol in a concentration between 5 and 10 mM. Finally, the lipids were mixed at desired molar ratios.

EMPTY LIPOSOMES: The preparation of empty liposomes was achieved by adding 0.166× PBS solution to the diluted alcoholic lipid mix, resulting in a final lipid concentration of 100 to 300 μM. For the lysolipid modified liposomes, linear mono-alkyl phosphates were added in the 0.166×PBS and were post-inserted to the liposomes.

SiRNA LOADED LIPOSOMES: The siRNA loaded liposomes were prepared by adding the siRNA solution; a buffer system containing 20 mM NaAc, 300 mM Sucrose and 100 mM HAc; to the alcoholic lipid mix in a volume resulting in a final alcohol concentration of 30%. The ratio (N/P) between the cationic charged lipids and the anionic charges from the siRNA was set between 1.5 and 5. A second solution containing 136 mM $Na_2HPO_4$ and 100 mM NaCl was added to the formed liposomal suspensions resulting in a final alcohol concentration of 10%. For the preparation of the lysolipids modified formulations, linear mono-alkyl phosphates were added in the second buffer.

The Size and Zeta potentials (ZP) of liposomes were measured using a HSA Zetasizer from Malvern Instruments Ltd. (Worcestershire, UK).

III. Example 3—In Vitro Assay for PLK1 Expression Knockdown

A reduction of Polo-Like-Kinase-1 (PLK1) induces mitotic arrest and apoptosis in proliferating tumor cell culture (Wolf et al., (1997) Oncogene. 14:543-549). Cell viability can be used as a read-out for transfection of siRNA targeting the PLK1 mRNA and as a marker for identifying cellular toxicity resulting from transfection with a scrambled siRNA. The siRNA sequences were designed as described in Haupenthal et al., (2007) International Journal of Cancer. 121:206-210.

Human cervical carcinoma cells (HeLa) were maintained in Dulbecco's Modified Eagle Medium (DMEM) supplemented with 10% fetal calf serum (FCS), penicillin and streptomycin at 37° C. under 5% $CO_2$. 6 or 24 hours prior to transfection, 3 to 5*10$^4$ HeLa cells were seeded into each well of a 96 well plate. After the cells reached a confluence of approximately 30% the liposomes were added to the cells. One hour prior to transfection, the formulations were diluted to the desired siRNA concentration in phosphate buffered saline (PBS) pH 7.4. A volume of 10 μl liposomes encapsulating PLK1 siRNA or a scrambled control were added to the cells. In addition, cells treated with PBS served as untreated control. Cell culture dishes were incubated for 72 hours at 37° C. under 5% $CO_2$. Cell proliferation was determined by using the CellTiter-Blue Cell Viability Assay (Promega GmbH, Mannheim, Germany) following the instructions of the manufacturer.

IV. Example 4—Zeta Potential Determination of Lysolipid Modified Liposomes

An example is provided here, demonstrating the creation of an anionic surface charge as a result of the insertion of anionic lysolipids in cationic liposomes. A series of empty cationic liposomes having varied ratios of cationic to anionic lipid (C:A) were prepared as in EXAMPLE 1. The lipids used for the preparation of these liposomes were the cation DOTAP, the anion DOPA and Cholesterol. In addition the same series of cationic liposomes were modified with 20 mol % of the lysolipid Hexadecyl phosphate. The liposomes had a final lipid concentration of 0.3 mM and their zeta potential values were determined. Examples of lipid compositions and their respectively zeta potential (ZP) values including standard deviations from three measurements are shown in Table 2.

It becomes apparent from the result presented in Table 2 that the cationic liposomes are modified with the lysolipid Hexadecyl phosphate. The addition of the anionic lysolipid shifts the zeta potential of the cationic liposomes from positive to negative values, creating thereby as expected an anionic surface charge. This is more striking for the liposomes prepared with cation to anion (C:A) ratios below 2.8.

TABLE 2

Mean values (±SD) of Zeta Potential of example lipid compositions

|  | C:A | Zeta Potential (mVolt) |  | Zeta Potential (mVolt) |
|---|---|---|---|---|
| DOTAP/DOPA | 3.2 | +19.8 (±2.8) | +Hexadecyl | −2.2 (±5.1) |
|  | 3.0 | +16.7 (±2.6) | Phosphate | −0.7 (±3.6) |
|  | 2.8 | +14.8 (±0.3) |  | −3.5 (±0.9) |
|  | 2.6 | +12.8 (±0.2) |  | −9.7 (±5.4) |
|  | 2.4 | +11.9 (±0.7) |  | −3.8 (±1.0) |
|  | 2.2 | +6.9 (±0.4) |  | −8.8 (±1.3) |
|  | 2.0 | +3.7 (±0.2) |  | −23.0 (±2.5) |
|  | 1.8 | +1.3 (±0.2) |  | −22.9 (±0.8) |

V. Example 5—Size Determination of Lysolipid Modified Formulations

An example is provided here, demonstrating an advantage of creating an anionic surface charge as a result of the insertion of anionic lysolipids in cationic liposomes. An exemplary series of siRNA loaded cationic liposomes having varied ratios of cationic to anionic lipid (C:A) were prepared as in EXAMPLE 1. The lipids used for the preparation of these liposomes were the cation DOTAP and the anion DOPA. Additionally, 10 mol % of the zwitterionic lipid POPC and 30 mol % Cholesterol were included in the lipid mixtures. The same series of cationic lipid formulations were also modified with 20 mol % of the lysolipid Hexadecyl phosphate. The liposomes had a final lipid concentration of 0.75 mM and their size was determined. The liposomal formulations were characterized with respect to their particle size.

Examples of lipid compositions formulated with siRNA and their respectively size values are illustrated in Table 3. All cationic RNAi formulations have size values above 1000 nm. This is an indication of unstable cationic bilayers, which form large aggregates. In comparison, modification of these cationic formulations with Hexadecyl phosphate leads to more stable formulations with size values between 400 and 500 nm.

TABLE 3

Size of example lipid compositions

|  |  | SIZE (nm) |  | SIZE (nm) |
|---|---|---|---|---|
| DOTAP/DOPA | 3.00 | 4075 | +Hexadecyl Phosphate | 494 |
| C:A | 2.75 | 48682 |  | 851 |
|  | 2.53 | 3493 |  | 476 |
|  | 2.33 | 2252 |  | 464 |
|  | 2.16 | 2026 |  | 437 |
|  | 2.00 | 5344 |  | 378 |

VI. Example 6—In Vitro Transfection Efficiency of Lysolipid Modified RNAi Formulations Several lysolipid modified RNAi formulations were tested and optimized for transfection of siRNA in vitro, in HeLa cells. A series of siRNA loaded liposomes having varied ratios of cationic to anionic lipid (C:A) were prepared using different cationic as well anionic lipids as in EXAMPLE 1. The liposomes contained 40 mol percentage Cholesterol and 20 mol percentage Hexadecyl phosphate. The liposomes were further supplied with 0.5 mol % DMPE-PEG2000. Examples of cationic and anionic lipids as well as their respective ratios are illustrated in Table 4 and 5. The final RNAi liposomal suspension had a final lipid concentration of 1 mM. Finally, the transfection efficiency of these lysolipid modified RNAi formulations was determined.

Each formulation was tested with 6 different siRNA concentrations ranging between 1-200 nM, and transfections were done in triplicates. Once added to the culture medium, the RNAi formulations were not removed from the cells. The fluorescence values from each transfection were normalized to the mean fluorescence value from mock-transfected cells, which were set as being 100%. The IC50 values derived from the data. Two values were used to evaluate the results of the assay: one is the effect of the control siRNA and the other the Plk1 siRNA treated cells in comparison to the control. The toxicity to a given cell line can be identified by transfecting cells with a negative control siRNA; also referred to as scrambled siRNA (SCR).

As it becomes clear from the data in table 4 and 5, a large number lysolipid modified liposomes can transfect the cells with siRNAs. Low IC50 values of the PLK1 siRNA were obtained with formulations comprising mixtures of DOTAP/DSPA, DOTAP/DPPA, DOTAP/DMPA, DOTAP/DOPA and DDAB/DOPA.

TABLE 4

Optimization results for the cationic lipids DOTAP and DDAB

|  |  | IC50 PLK-1 siRNA | | | IC50 SCR siRNA | | |
|---|---|---|---|---|---|---|---|
| Cation | Anion | C:A 3 | C:A 2.5 | C:A 2 | C:A 3 | C:A 2.5 | C:A 2 |
| DOTAP | DSPA | 33 | 36 | 41 | 173 | 105 | 154 |
|  | DPPA | 37 | 37 | 39 | 138 | 146 | 134 |
|  | DMPA | 36 | 75 | 56 | 200 | 147 | 138 |
|  | DLPA | 69 | 86 | 100 | 200 | 154 | 100 |
| DDAB | DSPA | 180 | 180 | 180 | 180 | 180 | 180 |
|  | DPPA | 147 | 180 | 172 | 180 | 180 | 180 |
|  | DMPA | 92 | 102 | 82 | 180 | 180 | 180 |
|  | DLPA | 67 | 73 | 69 | 180 | 180 | 180 |

TABLE 5

Transfection efficiency of various DOPA liposomes

| Lipid composition | | IC50 PLK-1 siRNA | IC50 SCR siRNA |
|---|---|---|---|
| DOTAP/DOPA | 3.00 | 36 | 96 |
| C:A | 2.75 | 33 | 99 |
|  | 2.53 | 20 | 69 |
|  | 2.33 | 18 | 70 |
|  | 2.24 | 19 | 71 |
|  | 2.16 | 21 | 67 |
|  | 2.00 | 19 | 85 |
| DDAB/DOPA | 3.00 | 13 | 180 |
| C:A | 2.53 | 4 | 81 |
|  | 2.24 | 4 | 79 |
|  | 2.00 | 9 | 180 |
| DOTMA/DOPA C:A 2.24 | | 36 | 76 |
| DODAP/DOPA C:A 2.24 | | 49 | 200 |

VII. Example 7—In Vivo Distribution of Lysolipid Modified RNAi Formulations

RNAi FORMULATIONS: Preparation of liposomes encapsulating a pool of two siRNAs was achieved by the alcohol injection method. The siRNAs were a 50% Cy5 labelled non-target siRNA and 50% Alexa-488 labelled non-target siRNA. Lipid mixtures were dissolved in isopropanol having a lipid concentration of 33 mM. The siRNA loaded liposomes were prepared by adding the siRNA solution, a buffer system containing 20 mM NaAc, 300 mM Sucrose and 100 mM HAc, to the alcoholic lipid mix in a volume resulting in a final alcohol concentration of 30%. The ratio (N/P) between the cationic charged lipids and the anionic charges from the siRNA was set to 2.7. A second solution containing 136 mM $Na_2HPO_4$ and 100 mM NaCl was added to the formed liposomal suspensions resulting in a final alcohol concentration of 10%. The resulting liposomal suspension was dialyzed against PBS to remove non-encapsulated siRNA and was subsequently concentrated. Table 6 summarizes the characteristics of the RNAi formulations, including also the lipid composition.

TABLE 6

Size, Polydispersity Index (PI) and Zeta Potential of Formulations

| Formulation | Lipid Composition | SIZE (nm) | PI | Zeta Potential (mVolt) |
|---|---|---|---|---|
| I | DDAB/DOPA C:A 2.24 + 0.25 mol % DMPE-PEG2 + 40 mol % Cholesterol + 20 mol % Hexadecyl Phosphate | 329 | 0.11 | −10.5 (±1.77) |
| II | DOTMA/DOPA C:A 2.24 + 0.25 mol % DMPE-PEG2 + 40 mol % Chololesterol + 20 mol % Hexadecyl Phosphate | 273 | 0.13 | −8.8 (±1.9) |

BIODISTRIBUTION STUDIES: In vivo siRNA distribution of the RNAi Formulations I and II of this invention was compared to that of the free siRNA in C57BL/6 male, 12-16 weeks of age, weighing 25-30 g (Charles River Laboratories, Inc., MA, USA) upon intratracheal and intranasal instillation. Saline was used as control group. Briefly, 9 µg of encapsulated siRNA in Formulation I and II or free siRNA were instilled intratracheally (FIG. 2) in a total volume of 40 µl. In addition, the biodistribution of these groups was compared after intranasal application (FIG. 3) of a total volume of 30 µl of 22 µg siRNA. The group size in each application was 5 mice.

24 h after the instillation, lungs were inflated through tracheotomy with a mixture of 4% PFA and OCT (2:1). Lungs were excised, submersed in 4% PFA overnight at 4° C. followed by an overnight incubation in 30% sucrose at 4° C. and processed for OCT embedding and sectioning. 10 µm histological sections were loaded onto poly-Lysine slide, washed with PBS and finally counterstained with nuclei dye DAPI. Images obtained using a Leica TCS SP5 confocal microscope with a dual (Tandem) Scanner.

FIG. 2 and FIG. 3 shows fluorescence microscopy images of lung tissues after intratracheal or intranasal administration of Cy5 labelled non-target siRNA (white colour), respectively. In comparison to free siRNA, both lysolipid modified Formulations I and II show markedly improved distribution of Cy5 labelled non-target siRNA in lung tissues and uptake by cells of the bronchiolar tree (brochial epithelium) and by cells of lung parenchyma such as macrophages. A weak fluorescence signal was obtained in lung tissues from mice treated with free siRNA. The lung tissue of mice that received PBS buffer did not show any fluorescence signal. The results correlate well with the findings from the flow cytometric analysis of Formulations I and II encapsulating Alexa 488 non-target siRNA (data not shown).

VIII. Example 8—Ecadherin Knockdown in Mice Lung Epithelium

RNAi FORMULATIONS: Preparation of liposomes encapsulating siRNAs or empty was achieved by the alcohol injection method. An active and a control siRNA were used in this study. a) Active siRNA: siRNA targeting Ecadherin (siCdh) and b) Control siRNA (siLuc). Lipid mixtures were dissolved in isopropanol having a lipid concentration of 20 mM. The siRNA loaded liposomes were prepared by adding the siRNA solution, a buffer system containing 20 mM NaAc, 300 mM Sucrose and 100 mM HAc, to the alcoholic lipid mix in a volume resulting in a final alcohol concentration of 30%. The ratio (N/P) between the cationic charged lipids and the anionic charges from the siRNA was set to 2.75. A second solution containing 136 mM Na2HPO4 and 100 mM NaCl was added to the formed liposomal suspensions resulting in a final alcohol concentration of 10%. The resulting liposomal suspension was dialyzed against PBSucrose to remove non-encapsulated siRNA and subsequent concentrated. Table 7 summarizes the characteristics of the RNAi formulations, including also the lipid composition and the siRNAs used in each formulation.

ANIMALS and qRT-PCR: Animals were sacrificed 48 h after a single siRNA application, and lungs were remove and instantly snap frozen in liquid nitrogen. Total RNA was isolated according to the TRI Reagent® protocol. RT-PCR was performed after DNase treatment of RNA and first-strand cDNA synthesis using the Promega kit according to the manufacturer's instructions. Ecadherin mRNA expression levels were analysed by quantitative real-time PCR and Changes in gene expression level were calculated by the $-2^{\Delta\Delta Ct}$ method and normalized to an endogenous reference.

TABLE 7

Context, Size, Polydispersity Index (PI) and Zeta Potential of Formulations

| Formulation | Lipid Composition | siRNAs | SIZE (nm) | PI | Zeta Potential (mVolt) |
|---|---|---|---|---|---|
| A | DDAB/DOPA C:A 2.24 + 0.25 mol % DMPE-PEG2 + 40 mol % Cholesterol + 20 mol % Hexadecyl-Phosphate | siCdh | 263 | 0.08 | −17.9 (±3.3) |
| B | | siLuc | 239 | 0.09 | −27.4 (±1.5) |
| C | | EMPTY | 247 | 0.07 | −21.3 (±3.1) |

RNAI STUDIES: The RNAi in vivo mRNA knockdown of Ecadherin was ascertained by comparing the RNAi Formulation A with the control Formulations (B and C) in C57BL/6 male, 12-16 weeks of age, weighing 25-30 g (Charles River Laboratories, Inc., MA, USA) upon intranasal instillation in a total volume of 40 µl. Saline was used as control group. In addition, free siRNA was also tested for in vivo mRNA knockdown of Ecadherin in total lung.

Figure 4:
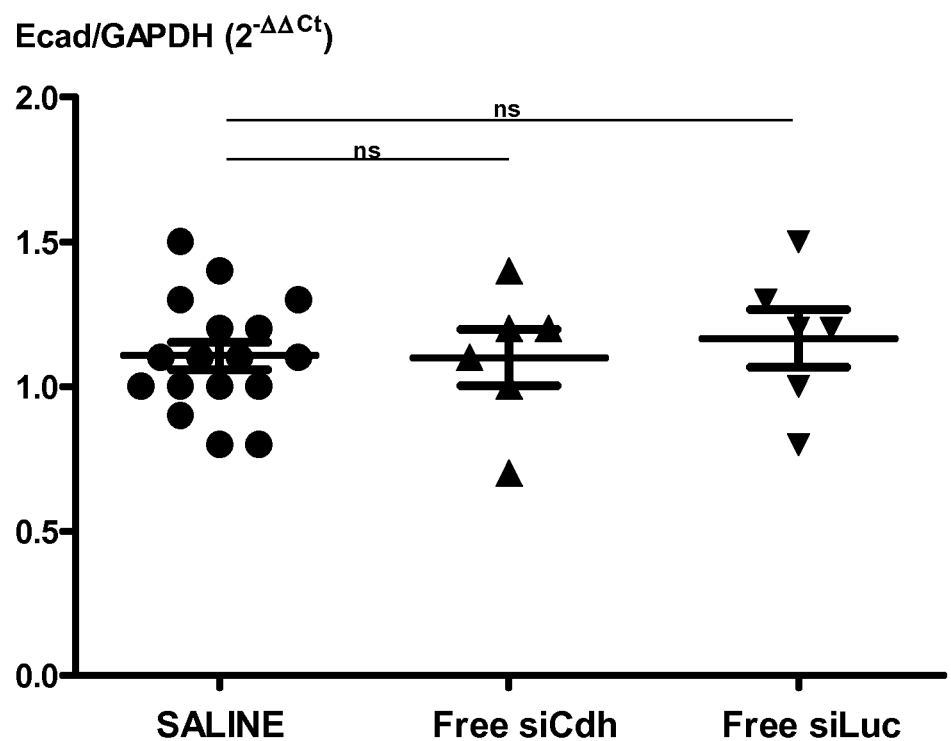
FIG. 4 shows Ecadherin mRNA levels in the lungs of mice 48 h after treatment with free siRNA targeting Ecadherin (free siCdh), with control siRNA (free siLuc) and saline according to Example 8 of the present invention.

The results in FIG. 4 shows Ecadherin mRNA levels in total lung 48 h after treatment with the free siRNA targeting Ecadherin compared to free control (siLuc) and saline. The injected dose for free siRNA was set to 1 mg/Kg. In comparison to the two control groups, free siRNA targeting Ecadherin (free siCdh) failed to down regulate mRNA levels of Ecadherin in lung epithelium.

Figure 5:
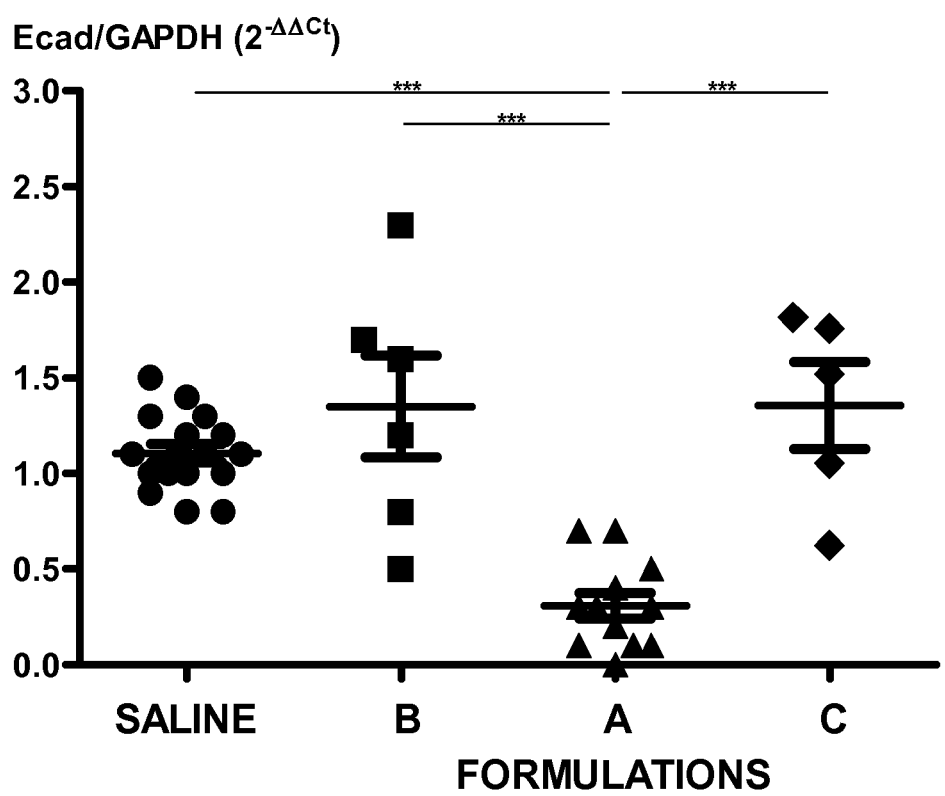
FIG. 5 shows Ecadherin mRNA levels in the lungs of mice measured 48 h after treatment with the lipid particles of the present invention containing siRNA targeting Ecadherin (Formulation A), control siRNA (Formulations B), empty lipid particles (Formulation C) and saline according to Example 8 of the present invention.
Figure 6:
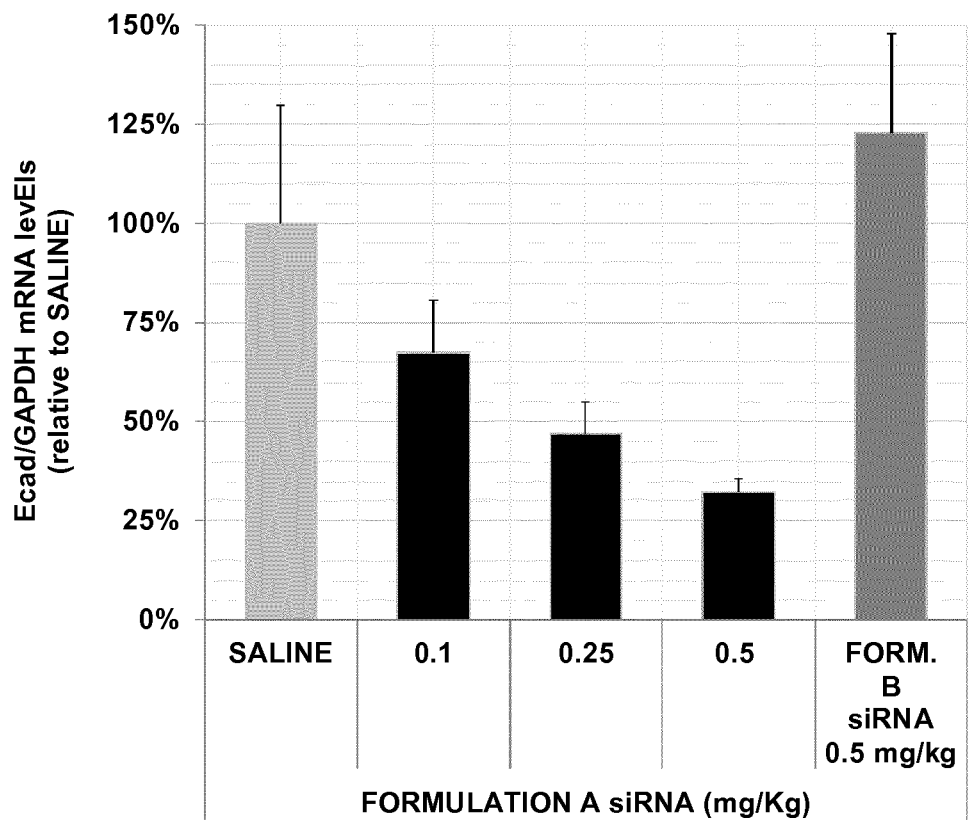
FIG. 6 shows Ecadherin mRNA levels in the lungs of mice measured 48 h following treatment with various dosage of siRNA targeting Ecadherin loaded in liposomes of the present invention. Results of Formulations A were compared with that obtained in mice treated with liposomes containing the control siRNA and saline according to Example 8 of the present invention.

In comparison to the free siCdh (FIG. 4) only the siRNA formulated in the liposomes enables reduction of Ecadherin mRNA levels in lung Epithelium. FIG. 5 summarizes two independent experiments. Ecadherin mRNA levels in the lung were measured after 48 h after treatment with the Formulations A, B, C and saline. The injected dose was set to 0.5 mg/Kg for formulations A and B. Formulation C was set to the same lipid concentration as in Formulations A and B. It is clearly apparent from the results that siRNA targeting Ecadherin formulated in lysolipid modified liposomes (Formulation A) resulted in greater mRNA down regulation of Ecadherin in comparison to the control Formulation B, C and saline FIG. 6 demonstrates Ecadherin mRNA levels in total lung 48 h after treatment with the Formulation A in comparison to Formulation B and saline. Targeting Ecadherin with a siRNA formulated in lysolipid modified liposomes resulted in dose dependent reduction of Ecadherin mRNA levels in total lung.

IX. Example 9—Safety Studies for Lysolipid Modified RNAi Formulations

FLUORESCENCE-ACTIVATED CELL SORTING (FACS): For preparation of lung single cell suspensions, mice were sacrificed with terminal bleeding and the lung was cleared from blood via PBS perfusion through the heart. Lungs were dissected into small pieces and digested with the following enzymes: 1 mg/ml Collagenase/Dispase mix, 2.4 U/ml Elastase and 0.2 mg/ml Dnase for 1.5 h at 37° C. with shaking. At the end of digestion, the cell suspension was filtered, and washed with HBSS-medium supplemented with 1% FCS, 1% penicillin/streptomycin and 5 M EGTA. Cell number and viability of the lung cells was determined with Trypan blue solution on a Neubauer chamber. Cell concentration was then adjusted at $1 \times 10^7$ cells/ml. For the FACS staining of lung cells, $1 \times 10^6$ cells in 100 μl were incubated with 10% Fc block (2.4G2 supernatant) for 10 min on ice. Subsequently, a mixture of the following antibodies was added: CD11b-Alexa488, Gr1-PE, CD45-PerCP-Cy5.5 and EpCAM-PECy7 and cells were incubated for 30 min at 4° C. in the dark. After staining, cells were washed once with HBSS-medium. Propidium iodide staining was added to the cell suspension to discriminate dead cells. Fluorescence was assessed by an FC500 flow cytometer (Beckman Coulter) and data were analyzed with the FlowJo software.

SAFETY STUDIES: RNAi formulations prepared in Example 8 were tested in a series of experiments for safety and tolerability. Animal studies and qRT-PCR were performed as described in Example 8. The injected dose for formulations was set to 0.5 mg/Kg siRNA. In order to test the lysolipid modified liposomes for immunostimulatory properties, ex vivo analysis of ISG15 and OAS1 mRNA levels was ascertained by comparing the Formulation A with Saline. Possible stimulation of TLRs would lead to IFN production resulting in induced expression of ISG15 (Interferon stimulated gene 15) and OAS1 (2'-5' Oligoadenylate synthetase 1). Subsequently, the safety of the lysolipid modified formulations was examined by analyzing with FACS the number of CD45$^+$ cells (Immune cells) and CD11b$^+$ Gr1$^+$ of CD45$^+$ cells (Neutrophils). Increased numbers of these two cell populations by comparing the Formulations A, B, C with saline would indicate signs of Inflammation caused by the liposomes of the present invention.

As demonstrated in FIG. 7, no significant changes in ISG15 and OAS1 mRNA levels were observed after treatment with siCdh formulated in lysolipid modified liposomes (Formulation A). In addition, the number of Immune cells and Neutrophils after treatment with Formulation A, B and C does not increased in comparison to the saline treated mice as shown in FIG. 8. It becomes apparent from the data of FIGS. 7 and 8 that the liposomes of the present invention are well tolerated in mice.

The invention claimed is:

1. A liposome comprising at least one lipid bilayer, wherein said at least one lipid bilayer comprises at least one type of cationic lipid, and optionally at least one type of neutral lipid, wherein an outermost layer of the at least one lipid bilayer of the liposome comprises at least one type of anionic lysolipid, wherein said at least one type of anionic lysolipid is negatively charged at a pH within a range of 4 to 8, and wherein the at least one type of anionic lysolipid is present in a sufficient concentration to provide the liposome with an anionic surface charge at a pH within a range of 4 to 8, or to provide the liposome with a net zero surface charge at a pH within a range of 4 to 8.

2. The liposome according to claim 1, wherein the at least one lipid bilayer further comprises at least one type of anionic lipid, and wherein the positive charges from the at least one type of cationic lipid exceed the negative charges from the at least one type of anionic lipid.

3. The liposome according to claim 2, wherein the at least one type of anionic lysolipid is present in a sufficient concentration to provide the liposome with the net zero surface charge at the pH within the range of 4 to 8.

4. The liposome according to claim 2, wherein the at least one type of anionic lysolipid is present in a sufficient concentration to provide the liposome the anionic surface charge at the pH within the range of 4 to 8.

5. The liposome according to claim 1, wherein the at least one type of anionic lysolipid is present in a sufficient concentration to provide the liposome with the net zero surface charge at the pH within the range of 4 to 8.

6. The liposome according to claim 1, wherein the at least one type of anionic lysolipid is present in a sufficient concentration to provide the liposome the anionic surface charge at the pH within the range of 4 to 8.

7. The liposome according to claim 1, wherein the at least one type of anionic lysolipid is selected from phosphates, phosphonates, sulfates or sulfonates.

8. The liposome according to claim 1, wherein the at least one type of anionic lysolipid is selected from at least one compound represented by the following formulas (I) to (VI)

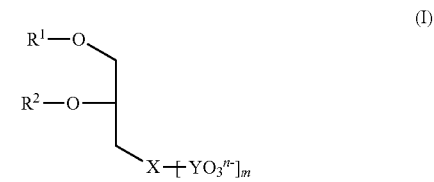

(I)

(II)

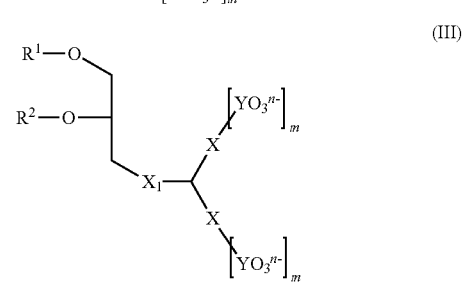

(III)

-continued

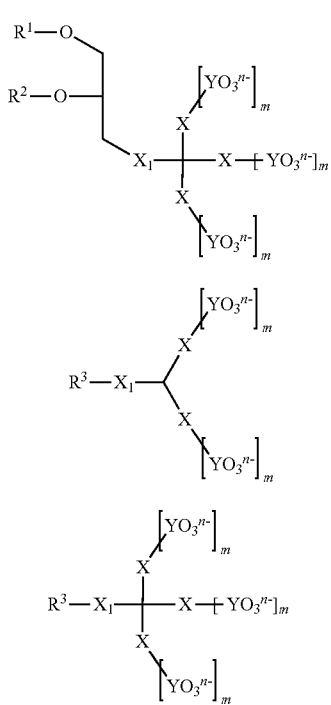

wherein:
X is absent or is selected from —$R^4$—, —$R^4$—O—, —O—$R^4$—, —$R^4$—NH—, —NH—$R^4$—, —$R^4$—C(O)—NH—, —C(O)—NH—$R^4$—, —$R^4$—C(O)—O—, —C(O)—O—$R^4$—, —$R^4$—O—C(O)—, —O—C(O)—$R^4$—, —$R^4$—O—C(O)—NH, —O—C(O)—NH—$R^4$—, —$R^4$—NH—C(O)—O—, —NH—C(O)—O—$R^4$—, —$(YO_3^{n-})_{1-5}$—$R^4$— or —O—$(YO_3^{n-})_{1-5}$—$R^4$—;
$X_l$ is absent or is selected from —$R^4$—, —$R^4$—O—, —O—$R^4$—, —$R^4$—NH—, —NH—$R^4$—, —$R^4$—C(O)—NH—, —C(O)—NH—$R^4$—, —$R^4$—C(O)—O—, —C(O)—O—$R^4$—, —$R^4$—O—C(O)—, —O—C(O)—$R^4$—, —$R^4$—O—C(O)—NH, —O—C(O)—NH—$R^4$—, —$R^4$—NH—C(O)—O—, —NH—C(O)—O—$R^4$—, —$(YO_3^{n-})_{1-5}$—$R^4$— or —O—$(YO_3^{n-})_{1-5}$—$R^4$—;
Y is P or S;
n is 1 or 2;
m is 1, 2, 3, 4, or 5;
$R^1$ and $R^2$ are selected from hydrogen, $C_5$-$C_{30}$ alkylcarbonyl, $C_5$-$C_{30}$ alkenylcarbonyl, $C_5$-$C_{30}$ alkynylcarbonyl, with the proviso that if one of $R^1$ or $R^2$ is hydrogen, the other group is not hydrogen;
$R^3$ is selected from $C_5$-$C_{30}$ alkyl, $C_5$-$C_{30}$ alkenyl, or $C_5$-$C_{30}$ alkynyl;
$R^4$ is absent or is selected from $C_1$-$C_{30}$ alkylene, $C_2$-$C_{30}$ alkenylene, or $C_2$-$C_{30}$ alkynylene.

9. The liposome according to claim 1, wherein the at least one lipid bilayer further comprises polymer-lipid conjugates or polymeric lipids.

10. The liposome according to claim 1, wherein the liposome further comprises one or more biologically active agents selected from nucleic acids, peptides, proteins or small molecules and wherein the one or more biologically active agents is (are) encapsulated within the liposome, bound to the inner or outer lipid layer of the liposome, and/or present between the inner and outer layers of the liposome.

11. The liposome according to claim 10, wherein the nucleic acid is an oligonucleotide selected from a short interfering RNA (siRNA), an antisense oligonucleotide, a double stranded RNA (dsRNA), a short hairpin RNA (shRNA), a decoy oligonucleotide, a ribozyme, DNAzyme, an aptamer, a microRNA, an anti-miR (antagomir) or a miR-mimic.

12. The liposome according to claim 11, wherein the nucleic acid comprises modified nucleosides.

13. The liposome according to claim 10, wherein the nucleic acid comprises modified nucleosides.

14. A method of delivering one or more biologically active agents to an epithelial surface of a mucous membrane, the method comprising transfecting an epithelial cell of the mucous membrane with the liposome according to claim 10.

15. A pharmaceutical formulation comprising the liposome according to claim 1 and one or more pharmaceutically acceptable excipient(s).

16. A method for the preparation of a liposome, comprising the following steps:
(a) preparing a liposome comprising at least one lipid bilayer, wherein said at least one lipid bilayer comprises at least one type of cationic lipid, and optionally at least one type of neutral lipid, and further optionally at least one type of anionic lipid;
(b) treating the liposome from step (a) with a solution of at least one type of anionic lysolipid, wherein said at least one type of anionic lysolipid is negatively charged at a pH within a range of 4 to 8, and wherein the at least one type of anionic lysolipid is present in a sufficient concentration to provide the liposome with an anionic surface charge at a pH within a range of 4 to 8, or to provide the liposome with a net zero surface charge at a pH within a range of 4 to 8, and
(c) optionally isolating the treated liposome of step (b).

17. The method according to claim 16, wherein the liposome prepared in step a) comprises at least one biologically active agent selected from nucleic acids, peptides, proteins or small molecules.

18. The method according to claim 17, wherein the nucleic acid is an oligonucleotide selected from a short interfering RNA (siRNA), an antisense oligonucleotide, a double stranded RNA (dsRNA), a short hairpin RNA (shRNA), a decoy oligonucleotide, a ribozyme, DNAzyme, an aptamer, a microRNA, an anti-miR (antagomir) or a miR-mimic.

19. The method according to claim 17, wherein the nucleic acid comprises modified nucleosides.

20. A method for the preparation of a liposome, comprising the following steps:
(a) preparing a liposome comprising at least one lipid bilayer, wherein said lipid bilayer comprises at least one type of anionic lipid, at least one type of cationic lipid, and optionally at least one type of neutral lipid, wherein the at least one type of cationic lipid is present in excess to the at least one type of anionic lipid;
(b) treating the liposome from step (a) with a solution of at least one type of anionic lysolipid, wherein said at least one type of anionic lysolipid is negatively charged at a pH within a range of 4 to 8, and wherein the at least one type of anionic lysolipid is present in a sufficient concentration to provide the liposome with an anionic surface charge at a pH within a range of 4 to 8, or to provide the liposome with a net zero surface charge at a pH within a range of 4 to 8, and
(c) optionally isolating the treated liposome of step (b).

21. The method according to claim 20, wherein the liposome prepared in step a) comprises at least one biologically active agent selected from the nucleic acids, peptides, proteins or small molecules.

22. The method according to claim 21, wherein the nucleic acid is an oligonucleotide selected from a short interfering RNA (siRNA), an antisense oligonucleotide, a double stranded RNA (dsRNA), a short hairpin RNA (shRNA), a decoy oligonucleotide, a ribozyme, DNAzyme, an aptamer, a microRNA, an anti-miR (antagomir) or a miR-mimic.

23. The method according to claim 21, wherein the nucleic acid comprises modified nucleosides.

* * * * *